US008975015B2

(12) United States Patent
McClay et al.

(10) Patent No.: US 8,975,015 B2
(45) Date of Patent: Mar. 10, 2015

(54) ANTIMICROBIAL COMPOUNDS

(75) Inventors: Kevin Rock McClay, Newton, PA (US); Robert Jon Steffan, Wrightstown, PA (US)

(73) Assignee: Shaw Intellectual Properties Holding, Inc., Baton Rouge, LA (US)

( * ) Notice: Subject to any disclaimer, the term of this patent is extended or adjusted under 35 U.S.C. 154(b) by 0 days.

(21) Appl. No.: 13/102,737

(22) Filed: May 6, 2011

(65) Prior Publication Data

US 2011/0212435 A1    Sep. 1, 2011

Related U.S. Application Data

(62) Division of application No. 12/898,806, filed on Oct. 6, 2010, now Pat. No. 7,973,065.

(60) Provisional application No. 61/249,396, filed on Oct. 7, 2009.

(51) Int. Cl.
| | | |
|---|---|---|
| *C12Q 1/26* | (2006.01) | |
| *C12Q 1/70* | (2006.01) | |
| *A61K 31/423* | (2006.01) | |
| *C07D 413/04* | (2006.01) | |

(52) U.S. Cl.
CPC ............ *A61K 31/423* (2013.01); *C07D 413/04* (2013.01); *C12Q 1/26* (2013.01)
USPC ................................................ 435/5; 435/25

(58) Field of Classification Search
None
See application file for complete search history.

(56) References Cited

U.S. PATENT DOCUMENTS

| | | | | |
|---|---|---|---|---|
| 7,364,747 | B1 * | 4/2008 | Haas .............................. | 424/405 |
| 2009/0221655 | A1 | 9/2009 | Josyula et al. | |

OTHER PUBLICATIONS

Gaballa et al. Microbiology (2011), 157, 3221-3231.*
Dorwald F. A. (Side Reactions in Organic Synthesis, 2005, Wiley: VCH, Weinheim p. IX of Preface.).*
"Monooxygenation," The Organic Chemistry of Enzyme-Catalyzed Reactions, Chapter 4. Presentation obtained from <http://faculty.washington.edu/gelb/Chp4.ppt> Accessed Mar. 9, 2013.*
Okuda et al., J. Phys. Chem. *A*, 2008, 112:11213-11222.
McClay, K., et al., "Toluene Monooxygenase-Catalyzed Epoxidation of Alkenes," Appl. Environ. Microbiol. 66, 2000.
Rattan, A., et al., "Multidrug-resistant *Mycobacterium tuberculosis*: molecular perspectives," Emer. Infec. Dis. 4, 1998.
Surendra, S.K., et al., "Multidrug-Resistant Tuberculosis," Chest 130, 2009.
World Health Organization (WHO), 2009, "Global tuberculosis control—epidemiology, strategy, financing," WHO Report 2009.
Zoller, "New recombinant DNA methodology for protein engineering," Curr. Opin. Biotech. 3, 1992.

Almquist et al., "Synthesis and Biological Activity of a Ketomethylene Analogue of a Tripeptide Inhibitor of Angiotensi Converting Enzyme," J. Med. Chem. 23, 1980.
Altman, L.K., "Drug-resistant TB Rising Sharply, WHO Warns," Herald Tribune, Feb. 26, 2008.
Altschul et al., "Basic Logical Alignment Search Tool," J. Mol. Biol. 215, 1990.
August, P.R., et al., "Sequence Analysis and Functional Characterization of the Violacein Biosynthetic Pathway from *Chromobacterium violaceum*," J Mol Microbiol Biotechnol 4, 2000.
Banerjee et al., "Extensively drug-resistant tuberculosis: new strains, new challenges," Expert Rev. Anti. Infect. Ther. 6(5), 2008.
Bao B., et al., "Bisindole alkaloids of the tosentin and hamacanthin classes from a marine sponge Spongosorities sp.," J Nat Prod 2007.
Broun et al., "Catalytic Plasticity of Fatty Acid Modification Enzymes Underlying Chemical Diversity of Plant Lipids," Science 282, 1998.
Byrne et al., "Sequence analysis of the gene cluster encoding toluene-3-monooxygenase from Pseudomonas pickettii PKO1," Gene 154, 1995.
Changsen, C., et al., "Improved Green Fhlorescent Protein Reporter Gene-Based Microplate Screening for Antituberculosis Compounds by Utilizing an Acetamidase Promoter," Antimicrob Agents Chemother 47, 2003.
Cho, S.H., et al., "Low Oxygen Recovery Assay (LORA) for High Throughput Screening of Compounds Against Non-Replicating *Mycobacterium tuberculosis*," Antimicrob Agents Chemother, Apr. 2007.
Cohn, D.L., et al., "Drug-Resistant Tuberculosis: Review of the Worldwide Situation and the WHO/IUATLD Global Surveillance Program," Clin. Infect. Dis. 24, Jan. 1997.
Collins, L., et al., "Microplate Alamar Bhue Assay Versus BACTEC 460 System for High-Throughput Screening of Compounds Against *Mycobacterium tuberculosis* and Mycobacterium avium," Antimicrob Agents Chemother 41, May 1997.
de Lorenzo et al., "Analysis of Pseudomonas gene products using lacl.sup.q/Ptrp-lac plasmids and transposons that confer conditional phenotypes," Gene 123, 1993.
Dooley, S.W., et al., "Multi-drug resistant tuberculosis (editorial)," Ann. Intern. Med 117, 1992.
Emirdag-Ozturk, S., et al., "Synthesis and antibacterial activity of egonol derivatives," Bioorg Med Chem 16, 2008.
Ensley et al., "Expression of Naphthalene Oxidation Genes in *Escherichia coli* Results in the Biosynthesis of Indigo," Science 222, 1983.
Feig et al., "Reactions of Non-Heme Iron(II) Centers with Dioxygen in Biology and Chemistry," Chem. Rev. 94, 1994.
Franzblau, S.G., et al., "Rapid, Low-Technology MIC Determination with Clinical *Mycobacterium tuberculosis* Isolates by Using the Microplate Alamar Blue Assay," J. Clin. Microb. Feb. 1998.
Giese et al., "The Role of Individual Cystein Residues in the Structure and Function of the v-sis Gene Product," Science 236, 1987.
Gillespie, D.E., et al., "Isolation of antibiotics turbomycin a and B from a metagenomic library of soil microbial DNA," Appl. Environ Microbiol. 68, 2002.

(Continued)

*Primary Examiner* — Alicia L Otton
(74) *Attorney, Agent, or Firm* — Riverside Law LLP

(57) ABSTRACT

The compounds disclosed herein are isoxazole derivatives that are useful as antimicrobial compounds, particularly as anti-bacterial compounds. The disclosed methods comprise incubating at least two different substrates in the presence of at least one oxygenase to provide the disclosed compounds, or to prepare and identify compounds that have antimicrobial activity.

10 Claims, No Drawings

(56) References Cited

OTHER PUBLICATIONS

Hann, M., et al., "On the Double Bond Isostere of the Peptide Bond: Preparation of an Enkephalin Analogue," J. Chem. Soc., Perkin Trans. I, 1982.

Haydon, D.J., et al., "An inhibitor of FtsZ with potent and selective anti-staphylococcal activity," Science 321, 2008.

Heifets, L.B., et al., "Pyrazinamide sterilizing activity in vivo against semidormant *Mycobacterium tuberculosis* populations," Am. Rev. Respir. Dis. 145, 1992.

Herrero et al., "Transposon Vectors Containing Non-Antibiotic Resistance Selection Markers for Cloning and Stable Chromosomal Insertion of Foreign Genes in Gram-Negative Bacteria," J Bact 172, 1990.

Hoemann, M.Z., et al., "Potent in Vitro Methicillin-Resistant *Staphylococcus aureus* Activity of 2-(1H-Indol-3-yl)quinoline Derivatives," Bioorg. Med. Chem. Lett. 10, 2000.

Hruby, V., "Conformational Restrictions of Biologically Active Peptides via Amino Acid Side Chain Groups (Minireview)," Life Sci. 31, 1982.

Hutchinson et al., "The Development of Site-directed Mutagenesis by Michael Smith," J Biol Chem 253, 1978.

Iseman, M.D., et al., "The increasing prevalence of resistance to antituberculosis chemotherapeutic agents: implications for global tuberculosis control," Curr. Clin. Top. Infect. Dis. 12, 1992.

Johnson et al., "The efficacy of certain anti-tuberculosis drugs is affected by binding to .alpha.-1-acid glycoprotein," Biomed. Chromatogr. 20, 2006.

Karlin, et al., "Methods for assessing the statistical significance of molecular sequence features by using general scoring schemes," Proc. Natl. Acad. Sci. USA, 87, 1990.

Karlin et al., "Applications and statistics for multiple high-scoring segments in molecular sequences," Proc. Natl. Acad. Sci. USA 90, 1993.

Kok et al., "Combining Localized PCR Mutagenesis and Natural Transformation in Direct Genetic Analysis of a Transcriptional Regulator Gene, pobR.dagger.," J Bact 179, 1997.

Kunkel, T., "Rapid and efficient site-specific mutagenesis without phenotypic selection," Proc Natl Acad Sci USA 82, 1985.

Lund et al., "Electron transfer reactions in the soluble methane monoosygenase of *Methylococcus capsulatus* (Bath)," Eur J Biochem 147, 1985.

Malakul et al., "Metal Toxicity Reduction in Naphthalene Biodegredation by Use of Metal-Chelating Adsorbents," Appl Environ Microbiol 64, 1998.

McClay, K. et al., "Biosensors for TCE Based on TCE-Induced Expression of Toluene 4-Monooxygenase from P. medocina KR1," Abstract K36, The 97th Annual Meeting of ASM, 1997.

McClay, K. et al., "Mutations of Toluene-4-Monooxygenase (T4MO) That Alter the Regiospecificity of Indole Oxidation and Lead to the Production of Novel Indigoid Pigments," Appl. Environ. Microbiol. 71, 2005.

Mermod et al., "Vector for Regulated Expression of Cloned Genes in a Wide Range of Gram-Negative Bacteria," J Bact 167, 1986.

Murrell, J., "Molecular genetics of methane oxidation," Biodegradation 5, 1994.

Myers, E., et al., "Optimal alignments in linear space," Comput. Applic. Biosci. 4, 1988.

Needleman, S. et al., "A General Method Applicable to the Search for Similarities in the Amino Acid Sequence of Two Proteins," J. Mol. Biol. 48, 1970.

Pikus, J.D., et al., "Recombinant toluene 4-monoosygenase. Catalytic and Mossbauer studies of the purified diiron and Rieske components of the four protein complex," Biochemistry 35, 1996.

Pikus, J.D., et al., "Changes in the regiospecificity of aromatic hydroxylation produced by active site engineering in the diiron enzyme toluene 4-monoosygenase," Biochemistry 36, 1997.

Pikus, J.D., et al., "Role of threonine 201 in toluene 4-monoosygenase catalysis," Biochemistry 35, 2000.

Pinner, R.W., et al., "Trends in infectious disease mortality in the United States," JAMA 275, 1996.

Rosenzweig et al., "Crystal Structures of the Methane Monooxygenase Hydroxylase From *Methylococcus capsulatus* (Bath): Implications for Substrate Gating and Component Internations," Proteins 29, 1997.

Shields et al., "Novel Pathway of Toluene Catabolism in the Trichloroethylene-Degrading Bacterium G4," Appl Environ Microbiol 55, 1996.

Spatola et al., "Structure-Activity Relationships of Enkephalins Containing Serially Replaced Thiomethylene Amide Bond Surrogates," Life Sci. 38, 1986.

Spellberg, B., et al., "Trends in antimicrobial drug development: Implications for the future," Antimicrob Res. Dev. 38., 2004.

Stover, C.K., et al., "A small-molecule nitroimidazopyran drug candidate for the treatment of tuberculosis," Nature, 2000.

Wackett and Gibson, "Degradation of Trichloroethylene by Toluene Dioxygenase in Whole-Cell Studies with Pseudomonas putida F1," Appl Environ Microbiol 54, 1988.

Whited and Gibson, "Separation of Partial Characterization of the Enzymes of the Toluene-4-Monooxygenase Catabolic Pathway in *Pseudomonas mendocina* KR1," J Bact 173, 1991.

World Health Organization (WHO), "Death by cause, sex, and mortality stratum in WHO regions, estimates for 2001," World Health Report, 2002.

Yen et al., "Cloning and Characterization of a *Pseudomonas mendocina* KR1 Gene Cluster Encoding Toulene-4-Monooxygenase," J Bacteriol 173, 1991.

Yen et al., "Identification of a New Gene, tmoF, in the *Pseudomonas mendocina* KR1 Gene Cluster Encoding Toulene-4-Monooxygenase," J Bacteriol 174, 1992.

Zhou et al., "The alkene monooxygenase from Xanthobacter Py2 is a binuclear non-haem iron protein closely related to toluene-4-monooxygenase," FEBS Lett 430, 1998.

Zoller and Smith, "Oligonucleotide-Directed Mutagenesis: A Simple Method Using Two Oligonucleotide Primers and a Single-Stranded DNA Template," DNA 3, 1984.

International Search Report for PCT/US10/51611, dated Feb. 14, 2011.

Vijey et al., "Synthesis and antimicrobial activities of 1-(5-substituted-2-oxoindolin-3-ylidene)-4-(substituted pyridin-2-yl)thiosemicarbozide," http://www.arkat-usa.org/get-file/23349; p. 187-189, 2008.

Taldone et al., "Discovery and development of heat schock protein 90 inhibitors," Bioorg. Med. Chem. Mar. 15, 2009, 17(6):2225-2235.

Boehm et al., "Novel inhibitors of DNA Gyrase: 3D structure based biased needle sceening, hit validation by biophysical methods, and 3D guided optimization. A promising alternative to random screening," J. Med. Chem. 2000, 43:2664-2674.

\* cited by examiner

```
SEQUENCE LISTING

<160> NUMBER OF SEQ ID NOS: 4

<210> SEQ ID NO 1
<211> LENGTH: 4644
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 1
aagcttttaa accccacagg cacggagaac aagaatatgg cgatgcaccc acgtaaagac      60
tggtatgaac tgaccagggc gacaaattgg acacctagct atgttaccga agagcagctt     120
ttcccagagc ggatgtccgg tcatatgggt atcccgctgg aaaaatggga aagctatgat     180
gagccctata agacatccta tccggagtac gtaagtatcc aacgtgaaaa ggatgcaggt     240
gcttattcgg tgaaggcggc acttgagcgt gcaaaaattt atgagaactc tgacccaggt     300
tggatcagca cttttgaaatc ccattacggc gccatcgcag ttggtgaata tgcagccgta     360
accggtgaag tcgtatggc ccgttttttca aaagcaccgg gaaatcgcaa catggctacg     420
tttggcatga tggatgaact cgcccatggc cagttacagc tgttttttccc gcatgaatac     480 tgtaagaagg atcgccagtt tgattgggca tggcgggcct atcacagtaa cgaatgggca     540
gccattgctg caaagcattt ctttgatgac atcattaccg gacgtgatgc gatcagcgtt     600
```

```
gcgatcatgt tgacgttttc attcgaaacc ggcttcacca acatgcagtt tcttgggttg    660
gcggcagatg ccgcagaagc aggtgactac acgtttgcaa acctgatctc cagcattcaa    720
accgatgagt cgcgtcatgc acaacagggc ggccccgcat acagttgct gatcgaaaac     780 ggaaaaagag aagaagccca aaagaaagtc gacatggcaa tttggcgtgc ctggcgtcta    840
tttgcggtac taaccgggcc ggttatggat tactacacgc cgttggagga ccgcagccag    900
tcattcaagg agtttatgta cgagtggatc atcggacagt cgaacgctc gttgatagat     960 ctgggcttgg acaagccctg gtactgggat ctattcctca aggatattga tgagcttcac    1020
catagttatc acatgggtgt ttggtactgg cgtacaaccg cttggtggaa ccctgctgcc    1080
ggggtcactc ctgaggagcg tgactggctg aagaaaaagt atccaggatg aataaacgt     1140 tggggtcgtt gctgggatgt gatcaccgaa aacgttctca atgaccgtat ggatcttgtc    1200
tctccagaaa ccttgcccag cgtgtgcaac atgagccaga taccgctggt aggtgttcct    1260
ggtgatgact ggaatatcga agttttcagt cttgagcaca atgggcgtct ttatcatttt    1320
ggctctgaag tggatcgctg gtattccag caagatccgg ttcagtatca aaatcatatg      1380
aatatcgtcg accgcttcct cgcaggtcag atacagccga tgactttgga aggtgccctc    1440
aaatatatgg gcttccaatc tattgaagag atgggcaaag acgcccacga ctttgcatgg    1500
gctgacaagt gcaagcctgc tatgaagaaa tcggcctgat aaattgagga atagaaaatg    1560
tcggcatttc cagttcacgc agcgtttgaa aaagatttct tggttcaact ggtagtggtg    1620
gatttaaatg attccatgga ccaggtagcg gagaaagttg cctaccattg tgttaatcgt    1680
cgtgttgctc ctcgtgaagg tgtcatgcgg gttcgaaagc atagatcaac tgagctattt    1740
ccacgggata tgaccatagc tgagagcggc cttaacccaa ctgaagtgat cgatgtggta    1800
ttcgaggagt agcgaaaatg agctttgaaa aatctgttc cctcgacgat atctgggtag     1860
gcgaaatgga gactttcgag acgtccgatg gtaccgaagt cttaatcgtc aacagtgaag    1920
agcatggagt gaaggcctac caggcgatgt gccccatca ggagattctg ttatctgaag      1980
gtagctacga aggtggagta attacatgcc gcgctcacct atggaccttc aatgacggaa    2040
cagggcatgg catcaaccca gatgactgtt gtcttgccga atatcctgta gaggtaaaag    2100
gcgatgatat ttacgtcagt acaaaaggca ttttaccgaa taaggcacac agctaaacct    2160
gcgctagttg ttaaatccca catcagcgaa gcggctggga aaagaaggat aatgtgatga    2220
gcacattggc tgatcaggct ttacataaca ataacgttgg accgattatc cgtgctggtg    2280
atctcgtgga accagtgatt gaaacagctg aaatcgataa tccggaaaaa gagatcacag    2340
ttgaagatag gcgggcttat gtacgcatcg cagcagaagg cgaactgata ttgactcgaa    2400
aaaccttgga agagcagttg ggtcgcccgt tcaacatgca ggaactagaa atcaatctgg    2460
cgtcctttgc aggacagatc caagccgacg aagaccagat tcgcttctac tttgataaaa    2520
ccatgtaagg agggcaccat gagctttgaa tccaagaaac cgatgcgtac atggagccac    2580
ctggccgaaa tgagaaagaa gccaagtgag tacgatattg tctcacgcaa gcttcactac    2640
agtaccaaca atcccgattc accctgggag ctgagccccg atagcccaat gaatctgtgg    2700
tacaagcagt accgtaacgc atcgccattg aaacacgata actgggatgc ttttactgat    2760
cctgaccaac ttgtataccg cacctacaac ctgatgcagg atggtcagga atcttatgtg    2820
cagagtctgt tcgatcaatt caatgagcgc gaacatgacc aaatggtgcg ggagggctgg    2880
gagcacacaa tggcccgctg ttattccccg ttgcgctatc tgttccactg cctgcagatg    2940
tcgtcggcct atgttcagca gatggcgccg gcgagcacaa tctcaaattg ctgcatcctt    3000
```

```
caaactgctg acagcctgcg atggttgacg cacaccgcct accgaacgca cgaactcagt    3060
cttacttatc cggatgctgg tttaggtgag cacgagcgag aactgtggga gaaagagccg    3120
ggttggcagg ggctgcgtga attgatggaa agcaactaa ctgcttttga ttggggagag     3180
gcttttgtca gtctaaattt ggtggtcaag ccaatgattg tcgagagtat tttcaaacca    3240
ctgcagcagc aagcatggga aaataacgat accttgcttc ctctgttgat tgacagtcag    3300
ctgaaagatg ccgagcgtca tagtcgttgg tcgaaagcac ttgtaaaaca tgcgctggaa    3360
aaccccgata tcacgctgt aattgaaggt tggattgaaa agtggcgccc cttggctgac     3420
agggcagctg aagcttacct gagtatgcta tctagcgaca ttttgcccgc tcaatatctt    3480
gagcgtagta cctcattgag ggcatccata cttacggtct gattacgcgc cgtttgggtc    3540
ctattggtgg gtcttcccct tcggcattgc tgaagggggct ttttagagac gttatctatg   3600
ttcaatattc aatcggatga tctcctgcac cattttgagg cggatagtaa tgacactcta    3660
cttagtgctg ctctacgtgc tgaattggta tttccatatg agtgtaactc aggagggtgc    3720
ggcgcatgta agatcgagct gcttgaggga gaggtctcta acctatggcc tgatgcacca    3780
ggattagccg cccgtgaact ccgtaagaat cgttttttgg cgtgccagtg caaaccatta    3840
tccgacctca aaattaaggt cattaaccgt gcggagggac gtgcttcaca tcccccaaa    3900
cgtttctcga ctcgagtagt tagtaagcgc ttcctctctg acgagatgtt tgagctgcga    3960
cttgaagcgg aacagaaagt ggtgttttca ccagggcaat attttatggt tgacgtgcct    4020
gaactcggca ccagagcata ctccgcggca aaccctgttg atggaaacac actaacgctg    4080
atcgtaaaag cagtgccgaa tgggaaggta tcctgcgcac tcgcaaatga aactattgaa    4140
acacttcagt tggatggtcc ttacgggctg tcagtattaa aaactgcgga tgaaactcaa    4200
tccgtctttta tcgctggggg gtcaggtatc gcgccgatgg tgtcgatggt gaatacgctg    4260
attgcccaag ggtatgaaaa accgattacg gtgttttacg gttcacggct agaagctgaa    4320
ctggaagcgg ccgaaaccct gtttgggtgg aaagaaaatt taaaactgat taatgtgtcg    4380
tcgagcgtgg tgggtaactc ggagaaaaag tatccgaccg gttatgtcca tgagataatt    4440
cctgaataca tggagggggct gctaggtgcc gagttctatc tgtgcggccc gccgcagatg    4500
attaactccg tccagaagtt gcttatgatt gaaaataaag taccgttcga agcgattcat    4560
tttgataggt tcttttaaaa ttaataagca atagttggtt ttagtagaat tttcagtggc    4620
gtaatgtcgg cgctaaggaa ctcc                                           4644
```

<210> SEQ ID NO 2
<211> LENGTH: 500
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 2

```
Met Ala Met His Pro Arg Lys Asp Trp Tyr Glu Leu Thr Arg Ala Thr
1               5                   10                  15

Asn Trp Thr Pro Ser Tyr Val Thr Glu Glu Gln Leu Phe Pro Glu Arg
            20                  25                  30

Met Ser Gly His Met Gly Ile Pro Leu Glu Lys Trp Glu Ser Tyr Asp
        35                  40                  45

Glu Pro Tyr Lys Thr Ser Tyr Pro Glu Tyr Val Ser Ile Gln Arg Glu
    50                  55                  60
```

```
Lys Asp Ala Gly Ala Tyr Ser Val Lys Ala Ala Leu Glu Arg Ala Lys
 65                  70                  75                  80

Ile Tyr Glu Asn Ser Asp Pro Gly Trp Ile Ser Thr Leu Lys Ser His
                 85                  90                  95

Tyr Gly Ala Ile Ala Val Gly Tyr Ala Ala Val Thr Gly Glu Gly
            100                 105                 110

Arg Met Ala Arg Phe Ser Lys Ala Pro Gly Asn Arg Asn Met Ala Thr
            115                 120                 125

Phe Gly Met Met Asp Glu Leu Arg His Gly Gln Leu Gln Leu Phe Phe
            130                 135                 140

Pro His Glu Tyr Cys Lys Lys Asp Arg Gln Phe Asp Trp Ala Trp Arg
145                 150                 155                 160

Ala Tyr His Ser Asn Glu Trp Ala Ala Ile Ala Ala Lys His Phe Phe
                165                 170                 175

Asp Asp Ile Ile Thr Gly Arg Asp Ala Ile Ser Val Ala Ile Met Leu
            180                 185                 190

Thr Phe Ser Phe Glu Thr Gly Phe Thr Asn Met Gln Phe Leu Gly Leu
            195                 200                 205

Ala Ala Asp Ala Ala Glu Ala Gly Asp Tyr Thr Phe Ala Asn Leu Ile
210                 215                 220

Ser Ser Ile Gln Thr Asp Glu Ser Arg His Ala Gln Gln Gly Gly Pro
225                 230                 235                 240

Ala Leu Gln Leu Leu Ile Glu Asn Gly Lys Arg Glu Ala Gln Lys
            245                 250                 255

Lys Val Asp Met Ala Ile Trp Arg Ala Trp Arg Leu Phe Ala Val Leu
            260                 265                 270

Thr Gly Pro Val Met Asp Tyr Tyr Thr Pro Leu Glu Asp Arg Ser Gln
            275                 280                 285

Ser Phe Lys Glu Phe Met Tyr Glu Trp Ile Ile Gly Gln Phe Glu Arg
            290                 295                 300

Ser Leu Ile Asp Leu Gly Leu Asp Lys Pro Trp Tyr Trp Asp Leu Phe
305                 310                 315                 320

Leu Lys Asp Ile Asp Glu Leu His His Ser Tyr His Met Gly Val Trp
            325                 330                 335

Tyr Trp Arg Thr Thr Ala Trp Trp Asn Pro Ala Ala Gly Val Thr Pro
            340                 345                 350

Glu Glu Arg Asp Trp Leu Glu Glu Lys Tyr Pro Gly Trp Asn Lys Arg
            355                 360                 365

Trp Gly Arg Cys Trp Asp Val Ile Thr Glu Asn Val Leu Asn Asp Arg
            370                 375                 380

Met Asp Leu Val Ser Pro Glu Thr Leu Pro Ser Val Cys Asn Met Ser
385                 390                 395                 400

Gln Ile Pro Leu Val Gly Val Pro Gly Asp Asp Trp Asn Ile Glu Val
            405                 410                 415

Phe Ser Leu Glu His Asn Gly Arg Leu Tyr His Phe Gly Ser Glu Val
            420                 425                 430

Asp Arg Trp Val Phe Gln Gln Asp Pro Val Gln Tyr Gln Asn His Met
            435                 440                 445

Asn Ile Val Asp Arg Phe Leu Ala Gly Gln Ile Gln Pro Met Thr Leu
            450                 455                 460

Glu Gly Ala Leu Lys Tyr Met Gly Phe Gln Ser Ile Glu Glu Met Gly
465                 470                 475                 480
```

```
Lys Asp Ala His Asp Phe Ala Trp Ala Asp Lys Cys Lys Pro Ala Met
                485                 490                 495

Lys Lys Ser Ala
            500

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 3
cggaattctt taaccccac aggcacgg                                          28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 4
gcgaattcga taatggtttg cactgcca                                         28
```

ANTIMICROBIAL COMPOUNDS

CROSS-REFERENCE TO RELATED APPLICATIONS

This application is a Divisional of U.S. application Ser. No. 12/898,806, filed Oct. 6, 2010, now U.S. Pat. No. 7,973,065, which claims the benefit of U.S. Provisional Application No. 61/249,396, filed Oct. 7, 2009, the entire contents of each of which are incorporated herein by reference.

BACKGROUND

Infectious diseases are illness in plants or animals caused by pathogenic microbial agents, including pathogenic viruses, bacteria, fungi, protozoa, and multicellular parasites, and aberrant proteins known as prions. These illnesses are often communicable because of transmission of the infectious replicating pathogenic agent from one person or species to another. Transmission of an infectious disease may occur through direct physical contact with infected individuals, through liquids, food, body fluids, contaminated objects, airborne inhalation, or vector-borne (e.g., insects etc.) distribution.

Despite the fact that infectious diseases, including Tuberculosis (TB), are the third-leading cause of death in the U.S. and the second-leading cause of death world wide, the FDA approval of new antibacterial agents decreased by 56% during the last 20 years. Between 1998 and 2004, only 9 new antimicrobials were approved by the FDA, and only two of these represented new antimicrobial mechanisms. In addition, a survey of the world's 15 largest pharmaceutical companies revealed that only 30 of 315 New Molecular Entity Drugs (NMEs) were identified as anti-infective agents, and only five of these were new antibacterial agents. None of the five represented novel mechanisms of action. The development of antimicrobial drugs for TB is even more dismal. After the introduction of rifampicin, no worthwhile anti-TB drug with a new mechanism of action has been developed in more than 30 years.

According to the WHO, there were 9.3 million incident cases of TB and 13.7 million prevalent cases of TB in 2007 (WHO, 2009). There also were 1.3 million deaths from TB among HIV-negative people in 2007, and an additional 450,000 deaths among HIV-positive TB cases—equivalent to 23% of deaths attributable to HIV. This equates to one death from TB every 20 seconds, which could be alleviated by effective antibiotic treatment. Because 86% of all cases occur in Africa and Asia, it is likely that many cases of TB go undiagnosed and/or untreated. Similar statistics are available for other pathogenic microbial agents including viruses, fungi, protozoans, and prions.

The development of drug resistance in pathogenic microorganisms has increased the urgency of the need to develop new antimicrobial compounds. The CDC recently reported that in American hospitals alone, healthcare-associated infections account for an estimated 1.7 million infections and 99,000 associated deaths each year. Of these infections 32 percent of all healthcare-associated infection are urinary tract infections, 22 percent are surgical site infections, 15 percent are pneumonia (lung infections), and 14 percent are bloodstream infections. Methicillin-resistant *Staphylococcus aureus* (MRSA), for example, is a type of staph bacteria that is resistant to beta-lactam antibiotics. These antibiotics include methicillin and other more common antibiotics such as oxacillin, penicillin, and amoxicillin. Although most MRSA infections are skin infections, the infections can spread to the blood stream, lungs, heart, bones, and joints, and they can be fatal because of the ineffectiveness of currently available antibiotics against the pathogen. Other common drug resistant bacteria include *Klebsiella pneumonia, Acinetobacter, Streptococcus pneumonia*, Drug-resistant TB (Tuberculosis), and Vancomycin-resistant Enterococci (VRE). Drug resistance also can arise in pathogenic fungi, protozoans, and viruses, thereby increasing the risk and severity of infections caused by these microbial agents.

SUMMARY

The compounds of the invention are useful as antimicrobial compounds, particular anti-bacterial compounds, and therefore address many of the needs discussed above. The compounds have the formula:

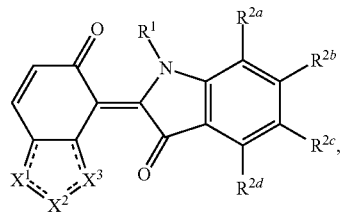

wherein: $X^1$-$X^3$ are independently selected from N, NH, O, S, CH, and $CH_2$; $R^1$ is hydrogen, hydroxy, or $C_1$-$C_4$ alkyl; $R^{2a}$-$R^{2d}$ are independently selected from hydrogen, hydroxy halogen, $C_1$-$C_4$ alkyl, $C_1$-$C_4$ alkoxy, cyano, and nitro; and each - - - is independently an optional bond; or a pharmaceutically acceptable salt thereof.

The method of treating a microbial infection in a subject in need thereof, comprises: administering to the subject a therapeutically effective amount of a compound having the formula:

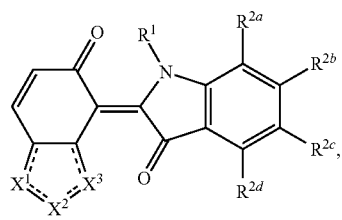

wherein: $X^1$-$X^3$ are independently selected from N, NH, O, S, CH, and $CH_2$; $R^1$ is hydrogen, hydroxy, or $C_1$-$C_4$ alkyl; $R^{2a}$-$R^{2d}$ are independently selected from hydrogen, hydroxy halogen, $C_1$-$C_4$ alkyl, $C_1$-$C_4$ alkoxy, cyano, and nitro; and each - - - is independently an optional bond; or a pharmaceutically acceptable salt thereof.

The method of preparing and identifying a compound that modulates the growth and/or replication of a microorganism, comprises: (a) incubating at least a first and second different compound in the presence of at least one oxygenase to provide a test compound; (b) contacting the microorganism with the test compound; and (c) determining a level of growth and/or replication of the microorganism; wherein a difference in the level of growth and/or replication of the microorganism as compared to the level in a control identifies the test compound as a compound that modulates the growth and/or replication of the microorganism.

DETAILED DESCRIPTION

As used herein, the term "substituted" is contemplated to include all permissible substituents of organic compounds. In a broad aspect, the permissible substituents include organic and inorganic substituents, including acyclic and cyclic, branched and unbranched, carbocyclic and heterocyclic, and aromatic and nonaromatic substituents. Illustrative substituents include, for example, those described below. The permissible substituents can be one or more and the same or different for appropriate organic compounds. For purposes of this disclosure, the heteroatoms, such as nitrogen and oxygen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Also, as used herein "substitution" or "substituted with" is meant to encompass configurations where one substituent is fused to another substituent. For example, an aryl group substituted with an aryl group (or vice versa) can mean that one aryl group is bonded to the second aryl group via a single sigma bond and also that the two aryl groups are fused, e.g., two carbons of one alkyl group are shared with two carbons of the other aryl group.

"Alkyl" is a branched or unbranched saturated hydrocarbon group of 1 to 40 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, octadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitro, nitrile, or thiol, as described below. A "lower alkyl" is an alkyl group with up to six carbon atoms, e.g., methyl, ethyl, propyl, butyl, pentyl, and hexyl.

"Alkyl" is generally used to refer to both unsubstituted alkyl groups and substituted alkyl groups; however, substituted alkyl groups are also specifically referred to herein by identifying the specific substituent(s) on the alkyl group. For example, the term "alkyl halide" specifically refers to an alkyl group that is substituted with one or more halides, e.g., fluorine, chlorine, bromine, or iodine. When "alkyl" is used in one sentence and a specific term such as "alkyl halide" is used in another, it is not meant to imply that the term "alkyl" does not also refer to specific terms such as "alkyl halide" and the like.

While a term such as "heteroaryl" refers to both unsubstituted and substituted heteroaryl moieties, the substituted moieties can, in addition, be specifically identified herein; for example, a particular substituted heteroaryl can be referred to as, e.g., an "alkyl heteroaryl." Similarly, a substituted alkenyl can be, e.g., an "alkenyl halide," and the like. Again, the practice of using a general term, such as "heteroaryl," and a specific term, such as "alkyl heteroaryl," is not meant to imply that the general term does not also include the specific term.

"Alkoxy" is an alkyl or cycloalkyl group bonded through an ether linkage; that is, an "alkoxy" group can be defined as —$OA^1$ where $A^1$ is alkyl or cycloalkyl as defined above. A "lower alkoxy" is an alkoxy group with up to six carbon atoms, e.g., methoxy, ethoxy, propoxy, butoxy, pentoxy, and hexoxy.

"Alkenyl" is a hydrocarbon group of from 2 to 60 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitro, nitrile, or thiol.

"Alkynyl" is a hydrocarbon group of 2 to 60 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitro, nitrile, or thiol.

"Aryl" is a group that contains any carbon-based aromatic group including, but not limited to, benzene, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, azide, nitro, nitrile, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

"Cycloalkyl" is a non-aromatic carbon-based ring composed of at least three carbon atoms. Examples of cycloalkyl groups include, but are not limited to, cyclopropyl, cyclobutyl, cyclopentyl, cyclohexyl, cyclooctyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, azide, nitrile, silyl, or thiol.

"Cycloalkenyl" is a non-aromatic carbon-based ring composed of at least three carbon atoms and contains at least one double bound, e.g., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitrile, or thiol.

"Halogen," or "halide" includes F, Br, I, and Cl.

The compounds of the invention have the formula:

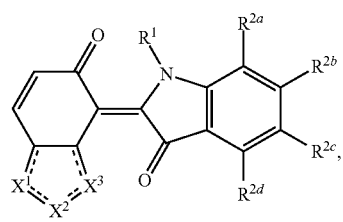

wherein $X^1$-$X^3$ are independently selected from N, NH, O, S, CH, and $CH_2$; $R^1$ is hydrogen, hydroxy, or $C_1$-$C_4$ alkyl; $R^{2a}$-$R^{2d}$ are independently selected from hydrogen, hydroxy halogen, $C_1$-$C_4$ alkyl, $C_1$-$C_4$ alkoxy, cyano, and nitro; and each - - - is independently an optional bond.

The compounds can be Z or E isomers. That is, the compounds can be either of the following isomers:

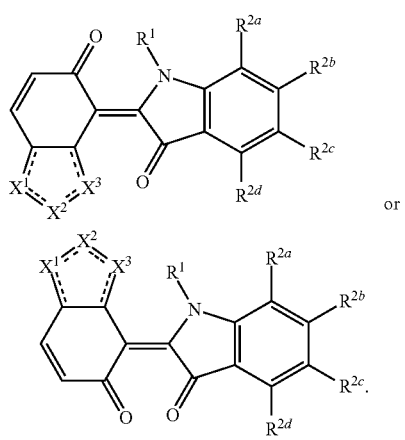

Although the compounds may be drawn in a Z or E configuration, both Z and E isomers are contemplated in each instance.

The $C_1$-$C_4$ alkyl substituent can be any straight chain or branched chain alkyl group having the indicated number of carbon atoms, such as methyl, ethyl, propyl, isopropyl, and n-butyl.

The $C_1$-$C_4$ alkoxy substituent can be any alkyl group of the indicated number of carbon atoms attached through an oxygen bridge, such as methoxy, ethoxy, propoxy, isopropoxy, n-butoxy, sec-butoxy, and tert-butoxy.

$R^{2a}$-$R^{2d}$ can be independently selected from hydrogen and halogen. The halogen can be Br, Cl, F, and I. In some examples, the halogen is selected from F and Cl.

In some examples, the compounds have the formula:

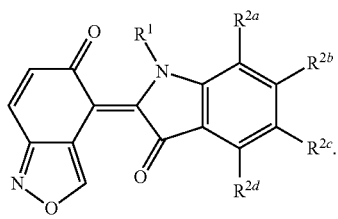

These compounds are prepared from indole and anthranil based substrates, as discussed below. Examples of such compounds include, without limitation, 4-(3-oxoindolin-2-ylidene)benzo[c]isoxazol-5(4H)-one; 4-(4-fluoro-3-oxoindolin-2-ylidene)benzo[c]isoxazol-5(4H)-one; 4-(4-chloro-3-oxoindolin-2-ylidene)benzo[c]isoxazol-5(4H)-one; 4-(5-fluoro-3-oxoindolin-2-ylidene)benzo[c]isoxazol-5(4H)-one; 4-(5-chloro-3-oxoindolin-2-ylidene)benzo[c]isoxazol-5 (4H)-one; 4-(6-fluoro-3-oxoindolin-2-ylidene)benzo[c]isoxazol-5(4H)-one; 4-(6-chloro-3-oxoindolin-2-ylidene)benzo[c]isoxazol-5(4H)-one; 4-(7-fluoro-3-oxoindolin-2-ylidene)benzo[c]isoxazol-5(4H)-one; and 4-(7-chloro-3-oxoindolin-2-ylidene)benzo[c]isoxazol-5(4H)-one.

In other examples, the compounds have the formula:

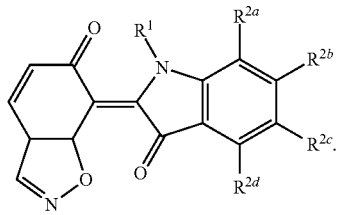

These compounds are prepared from benzoxazole and indole based substrates. Examples of such compounds include, without limitation, 7-(3-oxoindolin-2-ylidene)-7,7a-dihydrobenzo[d]isoxazol-6(3aH)-one; 7-(4-fluoro-3-oxoindolin-2-ylidene)-7,7a-dihydrobenzo[d]isoxazol-6(3aH)-one; 7-(4-chloro-3-oxoindolin-2-ylidene)-7,7a-dihydrobenzo[d]isoxazol-6(3aH)-one; 7-(5-fluoro-3-oxoindolin-2-ylidene)-7,7a-dihydrobenzo[d]isoxazol-6 (3aH)-one; 7-(5-chloro-3-oxoindolin-2-ylidene)-7,7a-dihydrobenzo[d]isoxazol-6(3aH)-one; 7-(6-fluoro-3-oxoindolin-2-ylidene)-7,7a-dihydrobenzo[d]isoxazol-6 (3aH)-one; 7-(6-chloro-3-oxoindolin-2-ylidene)-7,7a-dihydrobenzo[d]isoxazol-6(3aH)-one; 7-(7-fluoro-3-oxoindolin-2-ylidene)-7,7a-dihydrobenzo[d]isoxazol-6 (3aH)-one; and 7-(7-chloro-3-oxoindolin-2-ylidene)-7,7a-dihydrobenzo[d]isoxazol-6(3aH)-one.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

Pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutical compositions can also comprise adjuvants such as preserving, wetting, emulsifying, suspending agents, and dispensing agents. Prevention of the action of other microorganisms can be accomplished by various antifungal agents, for example, parabens, chlorobutanol, phenol, sorbic acid, and the like. It can also be desirable to include surfactants, binders, as for example, carboxymethylcellulose, alignates, gelatin, polyvinylpyrrolidone, sucrose, and acacia, humectants, as for example, glycerol, wetting agents, as for example, cetyl alcohol, and glycerol monostearate, adsorbents, as for example, kaolin and bentonite, and lubricants, as for example, talc, calcium stearate, magnesium stearate, solid polyethylene glycols, sodium lauryl sulfate, or mixtures thereof. Suitable suspending agents can include, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

The disclosed antimicrobial compositions can also comprise solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

The compounds and pharmaceutical compositions of the invention are useful in treating microbial infections. The activity of the compounds against various microbes are determined according to the methods described below in the Examples section. The microbial infection can be a variety of microbial infections, such as an infection of a Gram positive or Gram negative bacterium, a virus, or a protozoan.

Gram-positive bacterial infections that can be treated include, without limitation, infections of *M. tuberculosis* (including multi drug resistant TB and extensively drug resistant TB), *M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, *Propionibacterium acnes, Clostridium tetani, Clostridium perfringens, Clostridium botulinum,* other *Clostridium* species, and *Enterococcus* species.

Infections of gram-negative bacteria that can be treated include, without limitation, infections of *Pseudomonas aeruginosa,* other *Pseudomonas* species, *Campylobacter* species, *Vibrio cholerae, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species, *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, Escherichia hirae,* and other *Escherichia* species, as well as other *Enterobacteriacae, Burkholderia cepacia, Burkholderia pseudomallei, Francisella tularensis, Bacteroides fragilis, Fusobacterium nucleatum, Provetella* species, *Cowdria ruminantium, Klebsiella* species, and *Proteus* species.

The above examples of bacterial infections are not intended to be limiting, but are intended to be representative of a larger population including all bacterial infections that affect public health, as well as non-Gram test responsive bacterial infections. Examples of other bacterial infections include, but are not limited to, infections of *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia*

Rochalimaea, Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia, and Yokenella.

Specific examples of bacterial infections include, without limitation, infections of *M. smegmatis* or *B. subtilis*, *M. tuberculosis*, or multidrug resistant or extensively drug resistant *M. tuberculosis*. Other specific examples include *Salmonella typhimurium*, *Aeromonas hydrophila*, *Arcobacter butzleri*, *Bacillus cereus*, *Campylobacter jejuni*, *Escherichia coli*, *Listeria monocytogenes*, *Staphylococcus aureus*, *Pseudomonas fluorescens*, *Enterococcus* sp., *Clostridium difficile* and *Shewanella putrefaciens*.

"Drug resistant tuberculosis or TB" is also known as "Multidrug-resistant TB" (MDR TB) and is defined herein as TB that is resistant to at least two of the anti-TB drugs, isoniazid and rifampicin. These drugs are considered first-line drugs and are used to treat all persons with TB disease. "Extensively drug resistant TB" (XDR TB) is defined herein as a type of MDR TB. XDR TB is defined as TB which is resistant to isoniazid and rifampin, plus resistant to any fluoroquinolone and at least one of three injectable second-line drugs (i.e., amikacin, kanamycin, or capreomycin).

To treat microbial infection, the compounds and/or pharmaceutical compositions comprising the compounds are administered to a subject in need thereof, such as a vertebrate, e.g., a mammal, a fish, a bird, a reptile, or an amphibian. The subject of can be a human, non-human primate, horse, pig, rabbit, dog, sheep, goat, cow, cat, guinea pig, bat, or rodent. The term does not denote a particular age or sex. Thus, adult and newborn subjects, as well as fetuses, whether male or female, can be treated. The subject is preferably a mammal, such as a human. Prior to administering the compounds or compositions, the subject can be diagnosed with a need for treatment of microbial infection, such as a bacterial infection. The compounds and pharmaceutical compositions can also be administered to the subject prophylactically, i.e., to prevent a microbial infection.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disease or condition, such as cancer.

The therapeutically effective amount or dosage of the compound can vary within wide limits. Such a dosage is adjusted to the individual requirements in each particular case including the specific compound(s) being administered, the route of administration, the microbial infection being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

The compounds are prepared by incubating at least two different substrates in the presence of at least one oxygenase to provide the compound, according to the following scheme. Details of this procedure are provided in the Examples section below. The specific procedure discussed below can be altered by changing the at least two different starting substrates to provide different compounds of the invention.

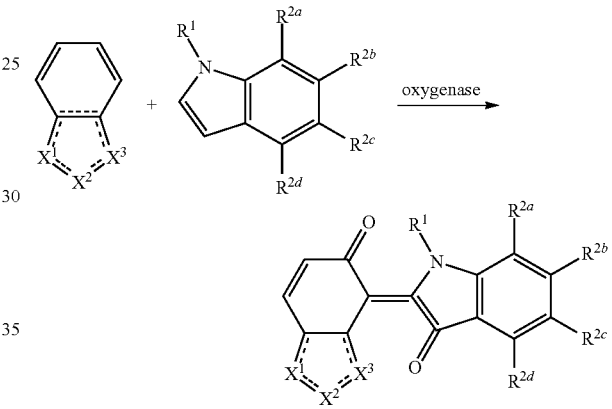

The oxygenase catalyzes the incorporation of one or both atoms of a molecule of oxygen ($O_2$) into the substrate. Monooxygenases catalyze the incorporation of one atom of oxygen into the substrate, the other oxygen being reduced to water. Aromatic oxygenases are non-heme diiron monooxygenase that oxidize a compound possessing an aromatic ring, such as, for example, toluene, benzene, and xylene or other aromatic ring-containing compounds, for example, naphthalene, anthracene, or indole. Cytochromes P450 monooxygenases belong to the superfamily of proteins containing a heme cofactor and, therefore, are hemoproteins. They also insert one atom of oxygen into an organic substrate, either aromatic or non-aromatic, while the other oxygen atom is reduced to water. Alkane monooxygenases are non-heme enzymes that insert a single atom of oxygen into an alkane or alkene molecule.

A variety of oxygenase enzymes can be used to prepare the compounds. For example, dioxygenases like methylene, naphthalene and toluene dioxygenases, including variants thereof, can be used. In other examples, variants of monooxygenases can be used. In a specific example, toluene monooxygenase, which oxidizes toluene at either the ortho-, meta-, or para-positions, can be used.

One exemplary species of toluene monooxygenase is toluene-4-monooxygenase (T4MO) produced by *Pseudomonas mendocina* KR1. The T4MO enzyme is a multi-component enzyme comprised of six functional peptides (TmoABC-DEF). The DNA sequences of Tmo A-E and Tmo F from *P.* mendocina KR1 are known. (Yen et al., "Cloning and characterization of a *Pseudomonas mendocina* KR1 gene cluster encoding Toluene-4-Monooxygenase," *J. Bacteriol.* 173:5315-27, 1991; Yen et al., *J. Bacteriol.* 174:7253-61, 1992). The complete 6 gene cluster has GeneBank accession number AY552601 and is listed as SEQ ID NO:1. The holozyme functions as an electron transport chain that shuttles electrons donated from NADH to the terminal sub-unit (TmoA). TmoA is a non-heme diiron-containing hydroxylase that facilitates the regio-specific para-hydroxylation of toluene through a reactive species of oxygen. The protein sequence of TmoA is listed as SEQ ID NO:2. The structure of the operon encoding the enzyme system, the enzyme amino acid sequence, and the basic catalytic mechanism of the enzyme are similar to several other diiron-containing enzymes including soluble methane monooxygenase (MMO) (Murrell, *Biodegradation* 5:145-59, 1994; Lund et al., *Eur. J. Biochem.* 147:297-305, 1985; Zhou et al., *FEBS Lett.* 430: 181-5, 1998), alkene monooxygenases (Zhou et al., *FEBS Lett.* 430:181-5, 1998), and toluene-2 and 3-monooxygenases (Shields et al., *Appl. Environ. Microbiol.* 55:1624-9, 1996; Byrne et al., "Sequence analysis of the gene cluster encoding toluene-3-monooxygenase form *Pseudomonas pickettii* PKO1," *Gene* 154:65-70, 1995). Therefore, the elucidation of the three dimensional structure of MMO (Rosenzweig et al., *Proteins* 29:141-52, 1997) has provided a tool for evaluating the potential structure of the other diiron monooxygenases for which the DNA sequence is known.

The oxygenase enzyme, such as the toluene monooxygenases, can be used in either its native or mutated form. In certain examples, the oxygenase is mutated to produce a modified enzyme (i.e., isoform). Changing the amino acid residues in the active site of the oxygenase is effective in producing diversity among compounds formed by the oxidation reaction. To determine the amino acids that can be mutated to effect diversity, an amino acid sequence alignment of several oxygenases is performed. The alignment can be performed manually based upon an initial alignment of conserved amino acids believed to act as iron ligands (Pikus et al., *Biochemistry* 36:9283-9, 1997), and previous alignments of some of the sequences performed by others (Zhou et al., *FEBS Lett.* 430:181-5, 1998; Pikus et al., *Biochemistry* 36:9283-9, 1997). Based on this sequence alignment, crystallographic studies of the MMO active site (Rosenzweig et al., *Proteins* 29:141-52, 1997), and hypotheses of others regarding the role of some active site amino acids, amino acid residues in a given monooxygenase can be selected as targets for site directed mutagenesis. Similarly, residues can be selected as targets for mutation in other oxygenases. The effect of such mutagenesis for monooxygenases is illustrated in Table 3, which presents the characterization of mutant T4MO isoforms discussed in the Examples section.

A variety of known molecular biology techniques can be used to mutate the gene(s) encoding an oxygenase, such as a non-heme diiron toluene monooxygenase. General methods for the cloning, expression and mutagenesis of recombinant molecules are described in Sambrook et al. (Molecular Cloning, A Laboratory Manual, 2nd edition, Cold Spring Harbor Laboratory Press, 1989) and in Ausubel et al. (eds.) (Current Protocols in Molecular Biology, Wiley and Sons, 1987), which are incorporated by reference herein for their teachings of cloning, expression and mutagenesis of recombinant molecules. Suitable techniques include mutagenesis using a polymerase chain reaction, gapped-duplex mutagenesis, and differential hybridization of an oligonucleotide to DNA molecules differing at a single nucleotide position. For a review of suitable codon altering techniques, see Kraik, "Use of Oligonucleotides for site Specific Mutagenesis," *Biotechniques* 12, 1985. Site-directed or site-specific mutagenesis procedures are disclosed in Kunkel, *Proc. Natl. Acad. Sci. USA* 82:488-92, 1985; Giese et al., *Science* 236:1315, 1987; U.S. Pat. No. 4,518,584; U.S. Pat. No. 4,959,314; Hutchinson et al., *J. Biol. Chem.* 253:6551, 1978; Zoller and Smith, *DNA* 3:479-88, 1984; Oliphant et al., *Gene* 44:177, 1986; Hutchinson et al., *Proc. Natl. Acad. Sci. USA* 83:710, 1986, which are all incorporated by reference for their teachings of site-directed or site-specific mutagenesis. In specific examples, PCR-based site-directed mutagenesis can be used (see Higuchi, "Using PCR to Engineer DNA," in PCR Technology: Principles and Applications for DNA Amplification, H. Erlich, ed., Stockton Press, Chapter 6, pp. 61-70, 1989).

A variety of microorganisms possess or can be modified to contain an oxygenase enzyme. In certain examples, the microorganism is a bacterial species that naturally possesses a monooxygenase or which is transformed with a DNA vector encoding a monooxygenase. Microorganisms that possess monooxygenases can be isolated from hydrocarbon contaminated soil by enrichment culturing, using techniques commonly used by those skilled in the art and previously described in the literature (McClay et al., *Appl. Environ. Microbiol.* 61:3479-81, 1995). Procedures that can be used to identify and isolate other strains of microorganisms that can be used in the practice of the methods disclosed herein are presented in the Examples section below. Examples of bacterial species containing non-heme diiron monooxygenases and that can be used in the methods disclosed herein include, for example, *Pseudomonas mendocina* KR1 (ATCC 55706); *Pseudomonas* sp. Strain ENVPC5; and *Pseudomonas* sp. Strain ENVBF1 (ATCC 55819); *B. cepacia* G4 (ATCC 53617); *B. picketti* Pk01, *Pseudomonas* sp. strain JS150, *Pseudomonas stutzeri* OX1. Other related organisms can be used also. A plasmid is deposited that also carries the T4MO enzyme system (ATCC 67671). Various exemplary strains and plasmids useful in the practice of the present invention are presented in Table 1.

TABLE 1

| Strains and Plasmids | Relevant Phenotype | Reference |
|---|---|---|
| *Pseudomonas mendocina* KR1 | T4MO | Whited and Gibson, *J Bact* 173: 3010-3016, 1991 |
| *Pseudomonas mendocina* ENVpmx1 | T4MO operon disrupted by lux and Tet$_r$ genes | McClay and Steffan, Abstract K36, p. 348, The 97th Annual Meeting of ASM, 1997 |
| *Pseudomonas pickettii* PKO1 | T3MO | Byrne et al., Gene 154: 65-70, 1995 |
| *Burkholderia cepacia* G4 | T2MO | Sheilds et al., *Appl Environ Microbiol* 55: 1624-1629, 1989 |
| *Pseudomonas putida* | TDO | Wackett and Gibson, *Appl Environ* |

TABLE 1-continued

| Strains and Plasmids | Relevant Phenotype | Reference |
|---|---|---|
| F1 | | *Microbiol* 54: 1703-1708, 1988 |
| *Acinetobacter calcoaceticus* ADP1 | Naturally competent, grows on ethanol | Kok et al., *J Bact* 179: 4270-4276, 1997 |
| *Pseudomonas putida* PPO200 | Cloning host, grows on ethanol | Malakul et al., *Appl Environ Microbiol* 64: 4610-4613, 1998 |
| *Burkholderia* sp strain ENVBF1 | T4MO | McClay et al., *Appl Environ Microbiol* 62: 2716-2722, 1996 |
| *Pseudomonas* sp strain ENVPC5 | T4MO | McClay et al., *Appl Environ Microbiol* 62: 2716-2722, 1996 |
| *E. coli* DH10B | Standard cloning host, auxotroph | Gibco Inc., Gaithersburg, MD |
| BL21(DE3) | Heterotrophic strain | New England Biolabs Inc., Beverly, MA |
| XL-1Red | Error prone DNA replication | Stratagene Inc., La Jolla, CA |
| S17-λ-pir | Mobilizes with plasmids Ori T | Herrero et al., *J Bact* 172: 6557-6567, 1990 |
| pUC18Not | Amp$^r$, standard cloning vector, MCS flanked by Not I sites | Herrero et al., *J Bact* 172: 6557-6567, 1990 |
| pUC18Sfi | Same as above except MCS is flanked by Sfi I sites | Herrero et al., *J Bact* 172: 6557-6567, 1990 |
| pLITMUS 2 | General cloning vector | New England Biolabs Inc., Beverly, MA |
| miniTn5 km2 | Transposon delivery plasmid. Kanamycin gene flanked by Sfi sites | deLorenzo et al., *Gene* 123: 17-24, 1993 |
| pTZR80 | Vector for inserting single copy of a cloned gene into the chromosome of *A. calcoaceticus*, under control of constitutive promoter | Kok et al., *J Bact* 176: 6566-6571, 1994 |
| pNM185 | Broad host range vector, Km$^r$, expression controlled by Xyl S | Mermod et al., *J Bact* 167: 447-454, 1986 |
| pVLT31 | Same as pNM185 except Tet$^r$, and use tac promoter controlled by lac I$^q$ | deLorenzo et al., *Gene* 123: 17-24, 1993 |
| pBR322 | General cloning vector, source of Tet$^r$ gene | Kok et al., *J Bact* 176: 6566-6571, 1994 |
| pRS184f series | Derivatives of pUC18Not that express T4MO and mutants | U.S. Pat. No. 7,169,591 |
| pRS202 series | Derivatives of pVLT31 that express T4MO and mutants | U.S. Pat. No. 7,169,591 |
| pRS202k series | Derivatives of pNM185 that express T4MO and mutants | U.S. Pat. No. 7,169,591 |

The isolation of an appropriate oxygenase can also involve the use of one or more other microorganisms in combination with one or more of the microorganisms described herein or microorganisms genetically modified to express a native or mutated oxygenase. For some applications, it can be desirable to introduce genes encoding an oxygenase into a microorganism that is especially suited to a given environment or which has certain growth requirements. Accordingly, microorganisms that have been transformed with a plasmid or other vector containing the gene(s) for an oxygenase, e.g., non-heme diiron monooxygenase, can be used. A procedure for transforming bacteria with an oxygenase gene (a toluene monooxygenase) is presented below in the Examples section. This procedure can be modified as necessary to introduce any cloned oxygenase into a given bacterial species. The oxygenase can be maintained within a host microorganism that is contacted with the substrates. However, it is also possible to isolate the enzyme from the microorganism and use the isolated and purified enzyme, if desired.

In specific examples, wild type T4MO (or other non-heme diiron containing monooxygenase) and any isoform thereof, where a mutation or set of mutations is created that changed the identity of the amino acids that make up the substrate binding pocket of the enzyme, are used. The nature of the mutations covered include any that result in an alteration of the identity of the amino acids that change the regio-specificity of the oxidations catalyzed by the enzyme or expand the substrate range of the enzyme so that the altered isoform can oxidize larger substrates that might otherwise be excluded from the active site (such as 4-aminoindole). Amino acids within the substrate binding pocket known to impact the substrate range and the regio-specificity of the T4MO enzyme (and related diiron monooxygenases) are as follows: I100, V102, G103, A107, Q141, F176, I192, F196, T201, N222, I224, and V227. Isoforms with mutations at one or more of these sites can be used. Some specific T4MO isoforms that can be used are shown in Table 2. The wild-type tmoA subunit is provided as SEQ ID NO:2

TABLE 2

| Isoform No. | Description |
| --- | --- |
| 1 | Wild type T4MO |
| 2 | I100A |
| 3 | I100C |
| 4 | I100V |
| 5 | V102T |
| 6 | G103I |
| 7 | G103L |
| 8 | G103V |
| 9 | A107C |
| 10 | A107S |
| 11 | A107T |
| 12 | Q141C |
| 13 | Q141E |
| 14 | F176A |
| 15 | F176L |
| 16 | I180F |
| 17 | L192M |
| 18 | F196I |
| 19 | F196Y |
| 20 | F196L |
| 21 | T201A |
| 22 | T201S |
| 23 | F205I |
| 24 | I224F |
| 25 | I227T |
| 26 | I227V |
| 27 | V102L:G103V |
| 28 | G103L:A107G |
| 29 | I100V:F196L |

As discussed above, numerous variants of oxygenases can be used. Protein variants and derivatives (i.e., isoforms) are well understood to those of skill in the art and can involve amino acid sequence modifications. Amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than from about 2 to about 6 residues are deleted at any one site within the protein molecule. These variants can ordinarily be prepared by site specific mutagenesis of nucleotides in the DNA encoding the protein, thereby producing DNA encoding the variant, and thereafter expressing the DNA in recombinant cell culture.

Techniques for making substitution mutations at predetermined sites in DNA having a known sequence are well known, for example M13 primer mutagenesis and PCR mutagenesis. Accordingly, recombinant technologies can be used for the production of the disclosed oxygenases. Amino acid substitutions are typically of single amino acid residues, but can occur at a number of different locations at once; insertions usually can be on the order of from about 1 to about 10 amino acid residues; and deletions can range from about 1 to about 30 residues. Deletions or insertions can be made in adjacent pairs, i.e., a deletion of 2 amino acid residues or insertion of 2 amino acid residues. Substitutions, deletions, insertions or any combination thereof may be combined to arrive at a final construct. Substitutional variants are those in which at least one amino acid residue has been removed and a different residue inserted in its place. Such substitutions generally are made in accordance with the following Table 3 and are known as conservative substitutions.

TABLE 3

| Original Residue Exemplary Conservative Substitutions, others are known in the art. |
| --- |
| Ala ↔ Ser |
| Arg ↔ Lys; Gln |
| Asn ↔ Gln; His |
| Asp ↔ Glu |
| Cys ↔ Ser |
| Gln ↔ Asn or Lys |
| Glu ↔ Asp |
| Gly ↔ Pro |
| His ↔ Asn or Gln |
| Ile ↔ Leu or Val |
| Leu ↔ Ile or Val |
| Lys ↔ Arg or Gln |
| Met ↔ Leu or Ile |
| Phe ↔ Met, Leu, or Tyr |
| Ser ↔ Thr |
| Thr ↔ Ser |
| Trp ↔ Tyr |
| Tyr ↔ Trp or Phe |
| Val ↔ Ile or Leu |

Substantial changes in function can be made by selecting substitutions that are less conservative than those in Table 3, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

The replacement of one amino acid residue with another that is biologically and/or chemically similar is known to those skilled in the art as a conservative substitution. A conservative substitution would be replacing one hydrophobic residue for another or one polar residue for another. The substitutions include combinations such as Gly, Ala; Val, Ile, Leu; Asp, Glu; Asn, Gln; Ser, Thr; Lys, Arg; and Phe, Tyr.

Such conservatively substituted variations of each explicitly disclosed sequence are included within the oxygenases disclosed herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g., Arg, can be accomplished, for example, by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the O-amino groups of lysine, arginine, and histidine side chains (Creighton, Proteins: Structure and Molecular Properties, W. H. Freeman & Co., San Francisco pp. 79-86, 1983, which is incorporated by reference herein for its material on post-translational derivatizations), acetylation of the N-terminal amine and, in some instances, amidation of the C-terminal carboxyl.

One way to define the variants, derivatives, and analogs of the oxygenases is through defining the variants, derivatives, and analogs in terms of homology/identity to specific known sequences. For example, SEQ ID NO:2 sets forth the particular sequence of wild type T4MO subunit A. Also disclosed are variants, derivatives, and analogs (i.e., isoforms) of these and other peptides and proteins herein disclosed which have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence similarity to the stated sequence.

Percent (%) sequence similarity or percent (%) sequence identity generally refer to the degree of identity or correspondence between different amino acid sequences of proteins or peptides that may or may not share a common evolutionary origin. Sequence identity can be determined using any of a number of publicly available sequence comparison algorithms, such as BLAST, FASTA, etc. To determine the percent identity between two amino acid sequences, the sequences are aligned for optimal comparison purposes. The percent identity between the two sequences is a function of the number of identical positions shared by the sequences (i.e., percent identity=number of identical positions/total number of positions (e.g., overlapping positions)×100). In one example, the two sequences are, or are about, of the same length. The percent identity between two sequences can be determined using techniques similar to those described below, with or without allowing gaps. In calculating percent sequence identity, exact matches are counted.

The determination of percent identity between two sequences can be accomplished using a mathematical algorithm. A non-limiting example of a mathematical algorithm utilized for the comparison of two sequences is the algorithm of Karlin and Altschul, *Proc. Natl. Acad. Sci. USA* 1990, 87:2264, modified as in Karlin and Altschul, *Proc. Natl. Acad. Sci. USA* 90:5873-5877, 1993. Such an algorithm is incorporated into the NBLAST and XBLAST programs of Altschul et al., *J. Mol. Biol.* 215:403, 1990. BLAST protein searches can be performed with the XBLAST program, score=100, wordlength=12, to obtain amino acid sequences homologous to protein sequences of the invention. Another non-limiting example of a mathematical algorithm utilized for the comparison of sequences is the algorithm of Myers and Miller, *CABIOS* 4:11-7, 1988. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. In one embodiment, the percent identity between two amino acid sequences is determined using the algorithm of Needleman and Wunsch (*J. Mol. Biol.* 48:444-53, 1970), using either a Blossum 62 matrix or a PAM250 matrix, a gap weight of 16, 14, 12, 10, 8, 6, or 4, and a length weight of 1, 2, 3, 4, 5, or 6. Sequence similarity can also be determined by inspection.

Numerous amino acid and peptide analogs can be incorporated into the disclosed oxygenases. For example, there are numerous D amino acids or amino acids which have a different functional substituent then the amino acids described above. The opposite stereo isomers of naturally occurring peptides, as well as the stereo isomers of peptide analogs. These amino acids can be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods Molec. Biol.* 77:43-73, 1991, Zoller, *Curr. Opin. Biotech.* 3:348-54, 1992; Ibba, *Biotech & Gen. Eng. Rev.* 13:197-216, 1995, Cahill et al., *TIBS* 14(10):400-3, 1989; Benner *TIB Tech* 12:158-63, 1994; Ibba and Hennecke, *Biotechnology* 12:678-82, 1994, all of which are incorporated by reference herein for their material related to amino acid analogs).

Molecules can also be synthesized that resemble the oxygenases disclosed herein, but which are not connected via natural peptide linkages. For example, peptide analogs can have linkages for amino acids or amino acid analogs that include —CH$_2$NH—, —CH$_2$S—, —CH$_2$—CH$_2$—, —CH=CH— (cis and trans), —COCH$_2$—, —CH(OH)CH$_2$—, and —CH$_2$SO— (These and others can be found in Spatola, in Chemistry and Biochemistry of Amino Acids, Peptides, and Proteins, B. Weinstein, eds., Marcel Dekker, New York, p. 267 (1983); Spatola, Vega Data (March 1983), Vol. 1, Issue 3, Peptide Backbone Modifications (general review); Morley, *Trends. Pharm. Sci.* pp. 463-8, 1980; Hudson et al., *Int. J. Pept. Prot. Res.* 14:177-85, 1979 (—CH$_2$NH—, —CH$_2$CH$_2$—); Spatola et al., *Life Sci.* 38:1243-9, 1986 (—CH$_2$S—); Hann, *J. Chem. Soc., Perkin Trans. I*, 307-14, 1982 (—CH=CH—, cis and trans); Almquist et al., *J. Med. Chem.* 23:1392-8, 1980 (—COCH$_2$—); Jennings-White et al., *Tetrahedron Lett.* 23:2533, 1982 (—COCH$_2$—); Szelke et al., EP 45665 CA (1982) (—CH(OH)CH$_2$—); Holladay et al., *Tetrahedron Lett.* 24:4401-4, 1983 (—CH(OH)CH$_2$—); and Hruby, *Life Sci.* 31:189-99, 1982 (—CH$_2$S—), each of which is incorporated by reference herein for its material regarding peptide analogs, mimetics, and non-peptide linkages). Peptide analogs can have more than one atom between the bond atoms, such as β-alanine, γ-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others. For example, D-amino acids and β-amino acids can be used to generate more stable peptides, because these amino acids are not recognized by peptidases. Systematic substitution of one or more amino acids of a consensus sequence with a D- or β-amino acid of the same type (e.g., D-lysine in place of L-lysine or β-alanine in place of alanine) can be used to generate more stable peptides. Cysteine residues can be used to cyclize or attach two or more peptides together. This can be beneficial to constrain peptides into particular conformations (Rizo and Gierasch, *Ann. Rev. Biochem.* 61:387, 1992).

The methods discussed above for preparing the compounds of the invention can also be used as a screening method to identify compounds that modulate the growth and/or replication of a microorganism. The method comprises: (a) incubating at least a first and second different compound in the presence of at least one oxygenase to provide a test compound; (b) contacting the microorganism with the test compound; and (c) determining a level of growth and/or replication of the microorganism; wherein a difference in the level of growth and/or replication of the microorganism as compared to the level in a control identifies the test compound as a compound that modulates the growth and/or replication of the microorganism.

The screening method uses monooxygenases as described above such as T4MO and its isoforms to catalyze the oxidation and subsequent polymerization of substrates such as indole and indole analogs (among many other substrates) to create compounds. Suitable substrates for use in the screening method are those that can be oxidized by an oxygenase. For example, suitable substrates are those that contain an unsaturated carbon-carbon bond.

Substrates for use in the disclosed methods can be represented by the general Formulas IA-C, which are substituted aryl, unsubstituted aryl, substituted heteroaryl, or unsubstituted heteroaryl groups.

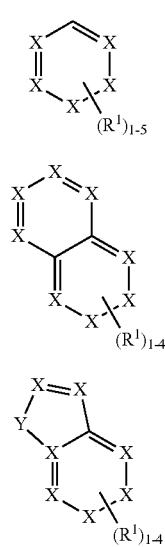

wherein each X is independently N, CH, or CR$^1$; Y is CH$_2$, O, or NH; and each R$^1$ is, independent of the others, hydrogen, hydroxy halide, hydroxy, amino, azide, nitro, amine, thiol, a substituted or unsubstituted alkyl, substituted or unsubstituted alkoxyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, aryl, or heteroaryl, with the proviso that when X is N, it is not substituted with an R$^1$ substituent and with the understanding that the valences of each X and Y are not violated.

Some additional examples of aryl and heteroaryl substrates that can be used in the screening method are shown below.

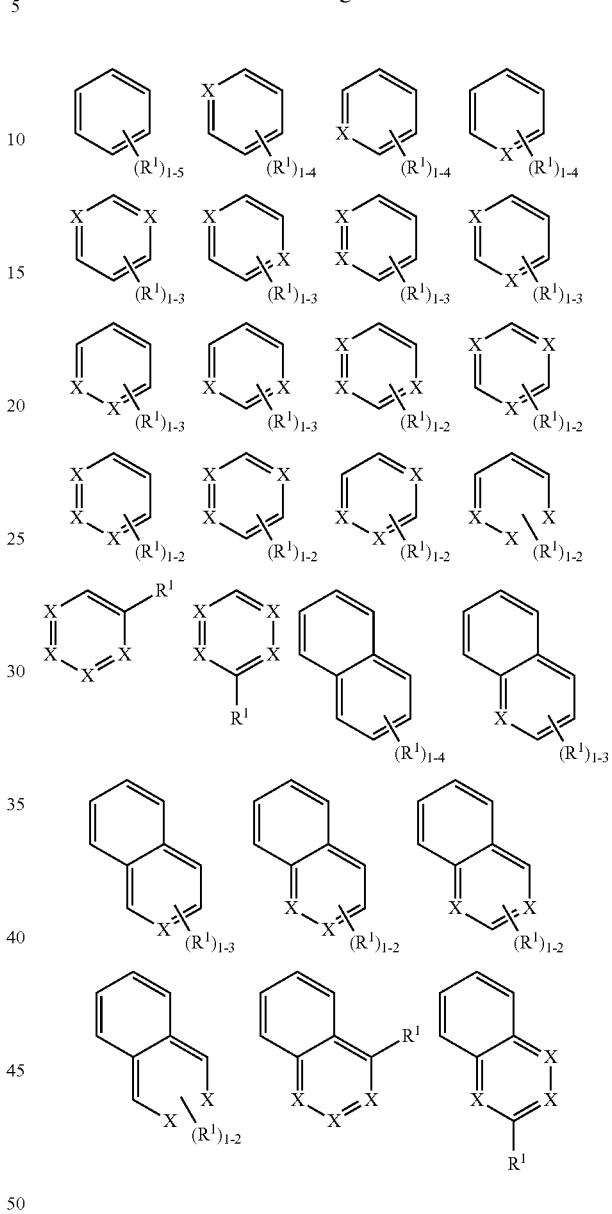

wherein X is N; and each R$^1$ is as defined before, with the proviso that X is not substituted with an R$^1$ substituent and with the understanding that the valences of each X are not violated.

Additional examples of suitable aryl and heteroaryl substrates are shown below.

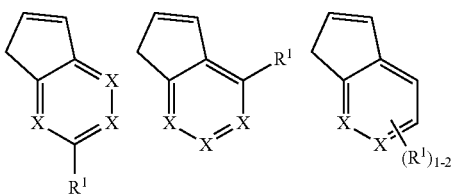

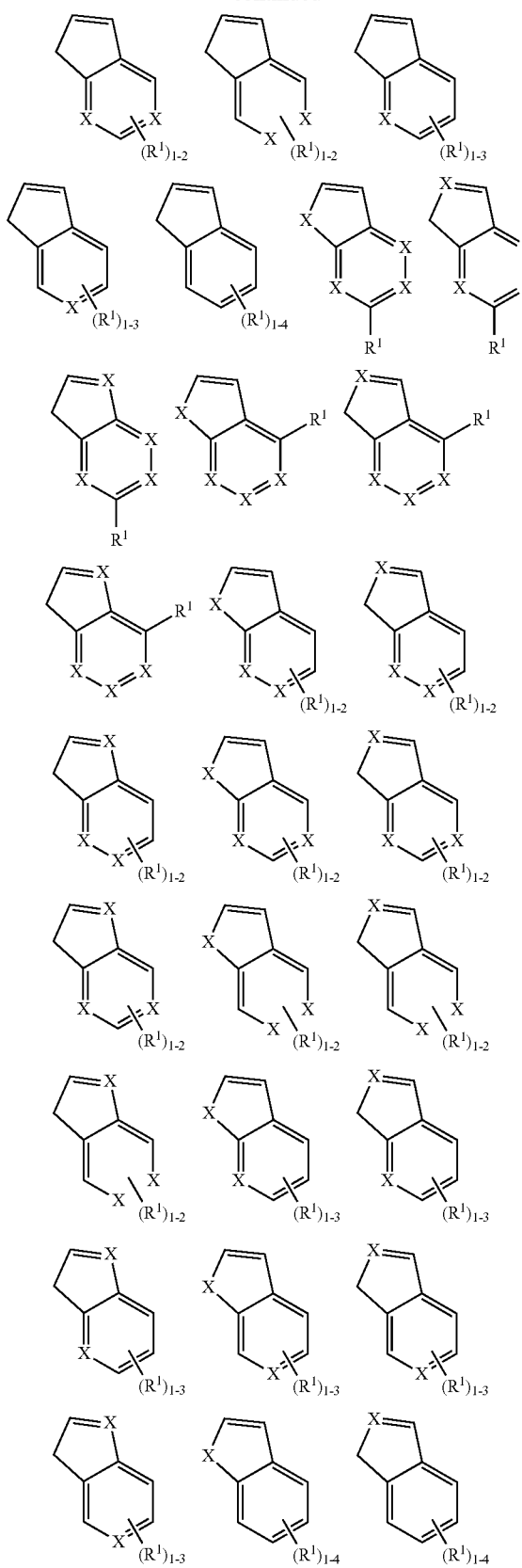

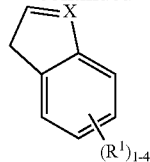

wherein X is N or NH; and R¹ is as defined before, with the proviso that X is not substituted with an R¹ substituent and with the understanding that the valences of each X are not violated.

Further examples of suitable substrates are shown below.

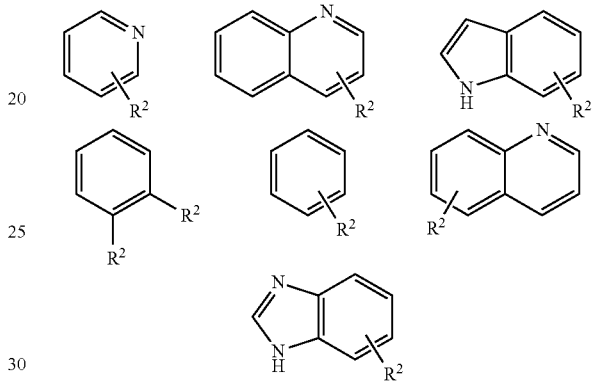

wherein $R^2$ is, independent of the others, H, alkyl, alkoxyl, halide, hydroxy, or amino.

Specific examples of substrates include, but are not limited to, substituted or unsubstituted aryl and heteroaryl compounds. The substrate can be indole, or an indole analog such as indene, isoindoline, 2-azaindole (indazole) 3-azaindole, 4-azaindole, 5-azaindole, 6-azaindole, 7-azaindole, benzimidazole, benzamidazoline, imidazopyridine, 4-azabenzamidazole, 5-azabenzamidazole, 6-azabenzamidazole, anthranil, benzisoxazole, benzoxazole, benzofuran, benzothiophene, benzothiazole, benzoisothiophene, quinoline, isoquinoline, quinozoline, and any isomer of the compounds listed above wherein a pendant hydrogen at any of the positions around the aromatic ring (positions 4-,5-,6-, or 7- for the indole family or positions 5-, 6-, 7-, or 8- for isomers belonging to the quinoline family) has been substituted with any of the following groups, —OH, —CH₃, —NH₂, —NO₂, F, Cl or Br.

Specific examples of combinations of substrates include, without limitation, the following.

| |
|---|
| Indole + Benzisoxazole |
| Indole + Benzothiazole |
| 4-Fluoroindole + Anthranil |
| Indole + Anthranil |
| 5-Fluoroindole + Anthranil |
| Indole + Benzisoxazole |
| 6-Fluoroindole + Anthranil |
| 4-Fluoroindole + Anthranil |
| Indole + Benzisoxazole |
| Indole + Benzoxazole |
| 5-Fluoroindole + Anthranil |
| 7-Fluoroindole + Anthranil |
| 5-Fluoroindole + Anthranil |
| Indole + Benzoxazole |
| 7-Fluoroindole + Anthranil |
| 5-Fluoroindole + Anthranil |

| |
|---|
| Indole + Benzoxazole |
| Indole + Benzisoxazole |
| Indole + Benzoxazole |
| Indole + Benzoxazole |
| Indole + Anthranil |
| Indole + Anthranil |
| 5-Chloroindole + Anthranil |
| 6-Chloroindole + Anthranil |
| 4-Chloroindole + Anthranil |
| 4-Chloroindole + Anthranil |
| Indole + Anthranil |
| 4-Chloroindole + Anthranil |
| 7-Fluoroindole + Anthranil |
| 5-Chloroindole + Anthranil |

The microorganism for which activity of the test compound can be determined includes a variety of microorganisms, such as a Gram positive or Gram negative bacterium, a virus, or a protozoan. Gram-positive bacteria that can be used and targeted include, without limitation, *M. tuberculosis* (including multi drug resistant TB and extensively drug resistant TB), *M. bovis*, *M. typhimurium*, *M. bovis* strain BCG, BCG substrains, *M. avium*, *M. intracellulare*, *M. africanum*, *M. kansasii*, *M. marinum*, *M. ulcerans*, *M. avium* subspecies *paratuberculosis*, *Staphylococcus aureus*, *Staphylococcus epidermidis*, *Staphylococcus equi*, *Streptococcus pyogenes*, *Streptococcus agalactiae*, *Listeria monocytogenes*, *Listeria ivanovii*, *Bacillus anthracis*, *B. subtilis*, *Nocardia asteroides*, and other *Nocardia* species, *Streptococcus viridans* group, *Peptococcus* species, *Peptostreptococcus* species, *Actinomyces israelii* and other *Actinomyces* species, *Propionibacterium acnes*, *Clostridium tetani*, *Clostridium perfringens*, *Clostridium botulinum*, other *Clostridium* species, and *Enterococcus* species.

Gram-negative bacteria that can be used in the screening method, without limitation, *Pseudomonas aeruginosa*, other *Pseudomonas* species, *Campylobacter* species, *Vibrio cholerae*, *Ehrlichia* species, *Actinobacillus pleuropneumoniae*, *Pasteurella haemolytica*, *Pasteurella multocida*, other *Pasteurella* species, *Legionella pneumophila*, other *Legionella* species, *Salmonella typhi*, other *Salmonella* species, *Shigella* species, *Brucella abortus*, other *Brucella* species, *Chlamydi trachomatis*, *Chlamydia psittaci*, *Coxiella burnetti*, *Escherichia coli*, *Neiserria meningitidis*, *Neiserria gonorrhea*, *Haemophilus influenzae*, *Haemophilus ducreyi*, other *Hemophilus* species, *Yersinia pestis*, *Yersinia enterolitica*, other *Yersinia* species, *Escherichia coli*, *Escherichia hirae* and other *Escherichia* species, as well as other *Enterobacteriacae*, *Burkholderia cepacia*, *Burkholderia pseudomallei*, *Francisella tularensis*, *Bacteroides fragilis*, *Fusobacterium nucleatum*, *Provetella* species, *Cowdria ruminantium*, *Klebsiella* species, and *Proteus* species.

The above examples of bacteria are not intended to be limiting, but are intended to be representative of a larger population including all bacteria that affect public health, as well as non-Gram test responsive bacteria. Examples of other species of bacteria include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania lgnavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Peptococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea, Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.*

Specific examples of bacteria include for which activity of the test compound can be determined include, without limitation, *M. smegmatis* or *B. subtilis*, *M. tuberculosis*, or multidrug resistant or extensively drug resistant *M. tuberculosis*. Other specific examples include *Salmonella typhimurium, Aeromonas hydrophila, Arcobacter butzleri, Bacillus cereus, Campylobacter jejuni, Escherichia coli, Listeria monocytogenes, Staphylococcus aureus, Pseudomonas fluorescens,* and *Shewanella putrefaciens.*

The methods disclosed above can also be used to make a library of chemical compounds. Generally, such a method comprises incubating a plurality of reaction vessels, wherein each reaction vessel contains two or more different substrates and one or more oxygenases. The substrates and oxygenases described above can used. This technique, referred to as "combinatorial biocatalysis," can be used to create compounds with activity against microbes, such as bacteria.

The combinatorial method involves the simultaneous reaction of multiple substrates with single or multiple enzymes, leading to the initial oxidation of the substrates followed by the spontaneous condensation of the reactive products to create a spectrum of products. A component of these methods is the use of a collection of substrate binding pocket mutants (isoforms) of a broad substrate range oxygenase, e.g., toluene-4-monooxygenase (T4MO), to expand the range of substrates that can be utilized and to diversify the spectrum of products produced.

The combinatorial method involves the simultaneous reaction of multiple substrates with single or multiple enzymes, leading to the initial oxidation of the substrates followed by the spontaneous condensation of the reactive products to create a spectrum of final products. A component of these methods is the use of a collection of substrate binding pocket mutants (isoforms) of a broad substrate range oxygenase, e.g., toluene-4-monooxygenase (T4MO), to expand the range of substrates that can be utilized and to diversify the spectrum of products produced. The inclusion of two separate oxygenase isoforms may be desirable because each enzyme isoform can have a different affinity for each substrate that comprises the intended final condensation product. Thus, if a single isoform preferentially activates substrate A to the exclusion of substrate B, the reactive products of substrate A and substrate B would not exist at the same time, and the only polymers produced in appreciable quantities would be A+A initially, then B+B when all substrate A had been consumed, with little or no A+B. However, if an enzyme isoform that preferentially activates substrate A and a second enzyme isoform preferentially oxidizes substrate B are employed in the same reaction, then the requisite reactive intermediates would exist at the same time. The product yield would be expanded to yield A+A, B+B as well as A+B. Accordingly, It is contemplated that a variety of di- and monooxygenases can be used in this method.

The wild type T4MO enzyme is able to hydroxylate a wide range of aromatic and aliphatic chemicals, and the substrate range has been expanded by creating isoforms with different substrate specificities and product distributions (McClay and Steffan, "Mutations of toluene-4-monooxygenase (T4MO) that alter the regiospecificity of indole oxidation and lead to the production of novel indigoid pigments," *Appl. Environ. Microbiol.* 71:5476-83, 2005; Pikus et al., "Recombinant toluene-4-monooxygenase. Catalytic and Mössbauer studies of the purified diiron and Rieske components of the four protein complex," *Biochemistry* 35:9106-19, 1996; Pikus et al., "Changes in the regiospecificity of aromatic hydroxylation produced by active site engineering in the diiron enzyme toluene 4-monooxygenase," *Biochemistry* 36:9283-9, 1997; Pikus et al., "Role of threonine 201 in toluene 4-monooxygenase catalysis," *Biochemistry* 39:791-9, 2000). These enzymes have been used to produce chiral epoxides (McClay et al., "Toluene monooxygenase-catalyzed epoxidation of alkenes," *Appl. Environ. Microbiol.* 66:1877-82, 2000) and novel derivatives of indole (McClay and Steffan, "Mutations of toluene-4-monooxygenase (T4MO) that alter the regiospecificity of indole oxidation and lead to the production of novel indigoid pigments," *Appl. Environ. Microbiol.* 71:5476-83, 2005).

The reaction products can then be purified or tested, e.g., for antimicrobial or antibacterial activity, as disclosed herein. In a specific example, the combinatorial library of compounds can be screened against other indications. In this regard, the combinatorial libraries of compounds comprise at least two (e.g., at least five, at least 10, at least 100, or more) different indole analogs and one or more oxygenases wherein each indole analog is prepared by incubating more than one different substrate and one or more oxygenase.

In addition to creating libraries, combinatorial biocatalysis can be used to create indole-derived compounds as agents against bacteria. This approach can be used to develop compounds with antimicrobial activity against MDR-TB and other drug resistant pathogenic bacteria (MRSA, VRE, etc.).

Genetic engineering was used to modify the active site of T4MO to alter indole oxidation (McClay and Steffan, "Mutations of toluene-4-monooxygenase (T4MO) that alter the regiospecificity of indole oxidation and lead to the production of novel indigoid pigments," *Appl. Environ. Microbiol.* 71:5476-83, 2005). The new isoforms (n=29) produced a wide range of pigments by differential oxidation of indole and conjugation of the resultant products. These experiments were expanded by incubating the isoforms with a suite of 12 additional indole-related bi-cyclic substrates. All of the compounds tested could be transformed by at least one of the 4 T4MO isoforms. In many cases, if both indole and a substituted indole analog were added as co-substrates, a new spectrum of products was created. The range of products derived from the simple pairing of two substrates is rich, demonstrating that multiple products can be derived from a single oxidation of indole analogs and the interaction of the products formed.

Thus, the combinatorial biocatalysis methods involve the incubation of a variety of substituted indole analogs, and mixtures thereof, with individual and multiple isoforms of T4MO to produce libraries of distinct but related compounds. The method can further involve the extraction of various fractions from the library, and purification of specific compounds from the library. The method can also involve the identification of at least one of the compounds in the library. Methods of using other oxygenase isoforms with combinations of two or more different substrates can also be used.

EXAMPLES

The following examples are not limiting of the scope of the present invention.

Example 1

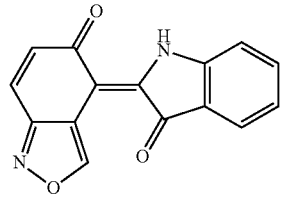 [SMILES: O=C1C=Cc2nocc2/C1=C1/Nc2ccccc2C1=O]

4-(3-oxoindolin-2-ylidene)benzo[c]isoxazol-5(4H)-one ("P1")

Production of P1 was initiated by picking colonies of *E. coli* BL21(DE3) carrying the desired T4MO isoform (I100V in this case) in the plasmid pNM185, and using them to inoculate 200 ml of BSM contained in a 1 liter baffled flask. Kanamycin (25 µg/ml) and glucose (0.5 g/L) were added to allow for growth and plasmid maintenance. The flasks were incubated at 30° C. with shaking (~100 RPM) overnight. The starter culture was then harvested via centrifugation in sterile containers (10,000×g for 10 minutes) and the supernatant discarded. The cell pellet was suspended in BSM in a minimal volume of BSM (20-40 ml) and distributed equally amongst 2-liter fermentation flasks containing 300 ml BSM, typical 4-6 flasks. The fermentation flasks were amended with kanamycin (25 µg/ml) and glucose (3 g/L). The flasks were incubated at 30° C. with shaking for 2 hours to allow cells to enter log phase growth and to build additional biomass. Following the acclimation period the flasks were flushed with 1 volume of pure oxygen and sodium benzoate (0.015 g/L) was added to stimulate the production of the cloned T4MO isoform. The induced culture was allowed to incubate for 2 hours prior to be flushed again with 1 volume of pure oxygen and 120 µl of each substrate (indole and anthranil) was added as 20% solutions in ethanol. The cultures were then returned to the shaker for an overnight incubation. The following day, the cells and adherent P1 were harvested via centrifugation (10 minutes at 8000×g). The resultant pellet was washed and suspended in distilled water (volume variable, approximately 1/40$^{th}$ original volume). 15 ml of the resultant suspension was added to 50-ml falcon tubes to which 12.5 ml of chloroform was added. The two phases were then vortexed vigorously until they were completely mixed and separated via centrifugation (10 minutes at 8000×g). The bottom solvent layer containing P1 was then collected and evaporated to concentrate the fermentation products. The extraction step was repeated until it was judged that 90% of the extractable material had been recovered.

It was determined that with the process described above, the pH in the fermentation flasks will drop as low as 3.5 during the overnight incubation. The formation of P1 decreases and the formation at least one yellow product, which is difficult to separate from P1, increases as the pH drops. If the production of P1 is desired to the exclusion of multiple products, it is beneficial to use 2×BSM stock to increase the buffering capacity and to bring up the pH from 7 to 7.5 or 8 using NaOH prior to sterilization. However, a greater diversity of chemical compounds, in somewhat lower yields can be produced by allowing the pH to drop during the course the transformation. The gradual change in physiochemical environment during fermentation favors the formation of the products that migrate more slowly on the TLC plates, suggesting that they are either larger or more polar than P1. Kanamycin slows the growth of the culture and can be omitted from the flasks during production if biomass is lower than desired at the outset of the production phase.

Higher oxygen content may favor production of P1. This may be another way to adjust the pH, because in a high oxygen atmosphere less acid is produced from glucose. Alternately, oxygen, which is needed for the reactive intermediate indoxyl to condense, may also be useful in an analogous reaction that leads to the formation of P1. In a low oxygen atmosphere, the reactive intermediates may combine in a different manner, to form trimers of indole-like substrates.

In place of fermentation flasks, a bioreactor can be used to grow the cells and induce the production of T4MO. The production of P1 and related compounds can also be carried out in bioreactors. To optimize production of P1 and minimize liquid handling, one can use 3 and 7.5 liter Applicon bioreactors that allow for greater control of pH and oxygen concentration.

To separate and purify P1, the dried chloroform extract was dissolved in the minimal volume of chloroform needed to dissolve the precipitate. The chloroform extract was then applied to a silica thin layer chromatography plate (20×20 cm, 2000 microns thick, Analtech Inc.) and allowed to dry. Once dry the TLC plates were resolved with a solvent comprised of 80% toluene and 20% acetone. The band containing P1 was excised and extracted with chloroform or acetone. The extracts were centrifuged to pellet any particulates and the supernatant decanted and evaporated to concentrate the product. A solution of 70% methanol or acetone and 30% water was added to the dried product. This solution was then injected onto either an C18 modified Onyx semi-preparative HPLC column (10×100 mm, Phenomonex Inc.) or a PrincetonSPHERE C18 column (21.2×150 mm, Princeton Chromotography Inc.). The compounds were eluted from the columns with a manually controlled solvent gradient of 50:50 methanol:water that was increased to 100% methanol. The pH of the water was adjusted to a pH of 5.5 with a 1 mM acetate buffer system. The fractions containing P1 were visually identified and manually collected as they eluted from the column. The collected fractions were concentrated under vacuum and analyzed via TLC and HPLC to assess the purity of the eluate. HPLC was conducted using the onyx column under an automated program that controlled the solvent ramp, flow (1-3 ml/minute) during a 40 minute run and monitored the eluant at four wavelengths (210, 280, 310, and 550 nm). Fractions found to contain more the one product by either method were discarded or subjected to subsequent rounds of purification depending on a subjective assessment of the concentration of P1 and the contaminants.

Purified P1 was characterized via HPLC UV/Vis and MS/MS. Purified P1 was dissolved in acetonitrile and separated on a ACE 3 C18 column (MAC-MOD Analytical Inc.) using a solvent system comprised of 10 mM ammonium acetate and acetonitrile, both containing 0.2% formic acid. The beginning concentration of acetonitrile was 5% and was ramped to 95% over 52 minutes with a constant flow of 0.6 ml/minute.

For NMR characterization, 2.4 mg of P1 was dissolved in 0.75 mL CDCl$_3$ (CIL DLM-29; 99.96% D); this solution was transferred into a 5-mm NMR tube (Wilmad 528PP). NMR spectra of the sample were obtained using a Bruker Avance III 500 spectrometer equipped with a BBFO/HF/D probe head. The sample was analyzed at ambient temperature by one-dimensional (1D) 1H and 13C NMR, by 1D 15N-filtered 1H NMR, and by two-dimensional (2D) {1H,1H} COSY, {1H, 1H} NOESY, {1H,13C} HSQC, {1H,13C} HMBC and {1H, 15N} HMBC spectroscopy. 1H Chemical shifts are referenced to TMS (tetramethylsilane), by calibrating the CHCl$_3$ residual solvent signal to 7.26 ppm. $^{13}$C Chemical shifts are referenced to TMS, by calibrating the position of the CD$_3$ multiplet of the solvent to 77.0 ppm. $^{15}$N Chemical shifts are referenced to external nitromethane (CH3NO2) at 0 ppm. The NMR results for P1 are shown in Table 4.

TABLE 4

$^{1}$H, $^{13}$C and $^{15}$N NMR Parameters for Compound P1.

| Hydrogen[a] | δ (ppm)[b] | | $^{3}J_{HH}$ (COSY) to | long-range J ($^{4}J_{HH}$ or $^{5}J_{HH}$) (COSY) to |
|---|---|---|---|---|
| H1 | 101.117 | (d) | — | H4 ($^{n}J = 0.95$ Hz) |
| H2 (exchangeable) | 12.411 | (br) | — | — |
| H3 | 6.756 | (d) | H4 (9.8 Hz) | — |
| H4 | 7.746 | (dd) | H3 (9.9 Hz) | H1 ($^{n}J = 0.95$ Hz) |
| H7 | 7077 | (d) | H8 (8.0 Hz) | — |
| H8 | 7.550 | (dt) | H7 (7.8 Hz), H9 (7.8 Hz) | H10 ($^{4}J = 1.3$ Hz) |
| H9 | 7.119 | (dt) | H8 (7.5 Hz), H10 (7.5 Hz) | H7 ($^{4}J = 0.8$ Hz) |
| H10 | 7.778 | (dd) | H9 (7.5 Hz) | H8 ($^{4}J = 1.0$ Hz) |
| Carbon[3] | | δ(ppm)[b] | $^{1}J_{HC}$ (HSQC) to | $^{2,3,4}J_{HC}$ (HMBC) to |
| C1 | (HC=O) | 157.42 | H1 (214 Hz) | — |
| C3 | (CH) | 133.69 | H3 | — |
| C4 | (CH) | 128.96 | H4 | — |
| C7 | (CH) | 112.60 | H7 | H9 ($^{3}J$) |
| C8 | (CH) | 137.24 | H8 | H10 ($^{3}J$), H9 ($^{2}J$) |
| C9 | (CH) | 123.23 | H9 | H7 ($^{3}J$) |
| C10 | (CH) | 125.75 | H10 | H8 ($^{3}J$) |
| Ca | (Cquat) | 153.76 | — | H1 ($^{3}J$), |

TABLE 4-continued

| | | | | |
|---|---|---|---|---|
| Cb | (Cquat) | 150.92 | — | H3 ($^3$J) H8 ($^3$J), H10 ($^3$J) |
| Cc | (Cquat) | 141.53 | — | — |
| Cd | (Cquat) | 119.81 | — | H7 ($^3$J), H9 ($^3$J) |
| Ce | (Cquat) | 112.31 | — | H1 ($^3$J), H4 ($^3$J) |
| Cf | (Cquat) | 101.79 | — | H3 ($^3$J) |
| Cg | (C=O) | 189.69 | — | H4 ($^3$J) |
| Ch | (C=O) | 188.78 | — | H10 ($^3$J) |

| Nitrogen$^3$ | | δ(ppm)$^b$ | $^1$J$_{HN}$ to | $^{2,3}$J$_{HN}$ (HMBC) to |
|---|---|---|---|---|
| Ny | (NH) | -332.4 | H2 (-99.5 Hz) | H7 (7.8 Hz) ($^3$J) |
| Nz | | ND | — | — |

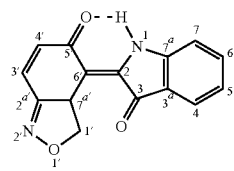

At various points during the extraction/purification process, crude extracts and HPLC fractions were tested for the ability to inhibit the growth of the test organism *Bacillus subtilis* 168 and *Mycobacterium smegmatis* mc 2 155. This was accomplished by drying the extracts down and suspending them in acetone. 5 μl drops of acetone, typically representing 2% of the fraction or extract, were applied to R2A agar plates and allowed to dry for ~1 hour. Dilute suspensions of the test organisms were then spread onto the agar plates, followed by an incubation of 24-48 hours at 30° C. The plates were then visually inspected to identify zones of growth inhibition around the spots that had been applied to the plate, providing a crude indication of which extracts and fractions contained active compounds. More sophisticated assays designed to assess the antibacterial activity of purified and semi-purified compounds had toward *Mycobacterium tuberculosis* (TB). The first of three biological parameters initially assessed determined the minimum inhibitory concentration (MIC) of the compounds against actively growing TB using the microplate alamar blue assay (MABA). The assay determined antibacterial activity of the compounds against non-replicating TB under low oxygen conditions (LORA). The third assay looked at the compounds toxicity toward mammalian cultured kidney cells from the African Green monkey (IC50).

The activity profile of P1 shows that it is active against both replicating TB (MABA MIC 0.49 μM) and non-replicating TB (LORA MIC 0.48 μM) which is comparable to the front line anti-TB drugs Rifampin (0.06 and 1.34 μM) and Isoniazid (0.56 and >128 μM), while having a favorable IC50 value of >50 ug/ml. P1 was also shown to be effective against strains of TB that are resistant to Rifampin (P1 MIC=0.239 μg/ml) Isoniazid (P1 MIC=0.138 μg/ml), Streptomycin (P1 MIC=1.011), Kanamycin (P1 MIC=0.148 μg/ml), and Cycloserine (P1 MIC=0.299), thus indicating the P1 has a unique mode of action and is effective against strains of TB that have evolved resistance from prior exposure to antibacterials. Compound P1 was also found to be active against *M. smegmatis*. (MIC 4.05 μg/ml).

Compound P1 was found to be stable in simulated gastric fluid. Table 5 shows the percentage of P1 remaining after exposure to simulated gastric fluid over time.

TABLE 5

| Time (minute) | % P1 | RD |
|---|---|---|
| 0 | 100 | 0 |
| 5 | 99.2 | 0.8 |
| 25 | 99.6 | 0.4 |
| 45 | 101.3 | -1.3 |
| 65 | 99.6 | 0.4 |
| 80 | 97.0 | 3.0 |
| 100 | 101.6 | -1.6 |
| 120 | 102.1 | -2.1 |
| 140 | 100.2 | -0.2 |

Compound P1 was also tested for stability in simulated intestinal fluid. The results are shown in Table 6.

TABLE 6

| Time (minute) | % P1 | RD |
|---|---|---|
| 0 | 100 | Control |
| 5 | 99.9 | 0.01 |
| 25 | 95.4 | 4.6 |
| 45 | 97.7 | 2.3 |
| 65 | 92.1 | 7.9 |
| 85 | 86.2 | 13.8 |
| 105 | 84.1 | 15.9 |
| 125 | 86.8 | 13.2 |
| 145 | 83.5 | 16.4 |

The half-life of P1 in mouse microsome was found to be about 3 or 4 minutes. The half-life of P1 in human microsome was found to be about 7 or 8 minutes.

Example 2

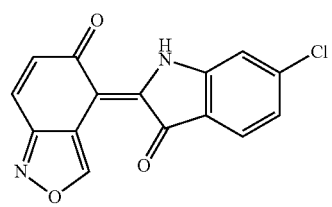 [SMILES: O=C1C=Cc2nocc2/C1=C1/Nc2cc(Cl)ccc2C1=O]

4-(6-chloro-3-oxoindolin-2-ylidene)benzo[c]isoxazol-5(4H)-one 4-(6-chloro-3-oxoindolin-2-ylidene)benzo[c]isoxazol-5 (4H)-one was prepared according to the procedure in Example 1 where the T4MO isoform I100V was incubated with 6-chloro-1H-indole and anthranil. The product was found to be active against replicating TB (MABA MIC 1.92 µM at 32-0.2 µM test concentration and 1.90 µM at 8-0.03 µM test concentration)

Example 3

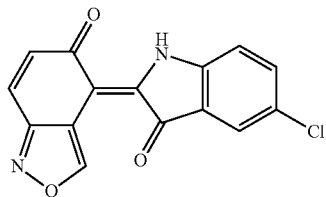 [SMILES: O=C1C=Cc2nocc2/C1=C1/Nc2ccc(Cl)cc2C1=O]

4-(5-chloro-3-oxoindolin-2-ylidene)benzo[c]isoxazol-5(4H)-one 4-(5-chloro-3-oxoindolin-2-ylidene)benzo[c]isoxazol-5 (4H)-one was prepared according to the procedure in Example 1 where the T4MO isoform I100V was incubated with 5-chloro-1H-indole and anthranil. The product was found to be active against replicating TB (MABA MIC 0.93 µM at 32-0.2 µM test concentration and 0.82 µM at 8-0.03 µM test concentration)and non-replicating TB (LORA MIC 0.83 µM)

Example 4

Screening Method

Feedstocks were incubated according to the procedure described in Example 1 where the T4MO isoform I100V was incubated with various substrates. Reaction products were screened for activity against both replicating and non-replication TB. The results are shown in Table 7.

TABLE 7

| MIC (ug/ml) | | | |
|---|---|---|---|
| MABA | LORA | IC50 | Feedstock |
| 0.576 | 5.444 | 46.21 | 4-Fluoroindole + Anthranil |
| 7.661 | >10 (70%) | 22.67 | 4-Fluoroindole + Anthranil |
| 3.891 | >10 (81%) | 42.81 | 4-Fluoroindole + Anthranil |
| 9.529 | >10 (0%) | 23.51 | Indole + Benzisoxazole |
| 10 | >10 (0%) | >50 (6%) | Indole + Benzothiazole |
| 4.734 | >10 (80%) | >50 (17%) | 4-Fluoroindole + Anthranil |
| 0.133 | 4.079 | 11.8 | Indole + Anthranil |
| 0.15 | 2.948 | >50 (0%) | 5-Fluoroindole + Anthranil |
| 9.916 | >10 (0%) | >50 (0%) | Indole + Benzisoxazole |
| 0.304 | 2.452 | >50 (0%) | 6-Fluoroindole + Anthranil |
| 0.212 | 0.958 | 10.81 | 4-Fluoroindole + Anthranil |
| 3.921 | >10 (32%) | 44 | Indole + Benzisoxazole |
| 1.94 | >10 (16%) | 41.74 | Indole + benzoxazole |
| 3.983 | >10 (33%) | 42.57 | 5-Fluoroindole + Anthranil |
| 4.144 | >10 (43%) | 43.48 | 7-Fluoroindole + Anthranil |
| 1.822 | 7.997 | <3.125 | 5-Fluoroindole + Anthranil |
| 0.61 | >10 (36%) | >50 (18%) | Indole + Benzoxazole |
| 1.193 | >10 (38%) | >50 (4%) | 7-Fluoroindole + Anthranil |
| 4.726 | >10 (35%) | >50 (0%) | 5-Fluoroindole + Anthranil |
| 0.074 | 4.384 | 11.01 | Indole + Benzoxazole |
| 0.136 | 7.684 | 18.46 | Indole + Benzisoxazole |
| 0.105 | 4.868 | 11.69 | Indole + Benzoxazole |
| 0.502 | >10 (85%) | >50 (31%) | Indole + Benzoxazole |
| 0.177 | 3.78 | 21.28 | Indole + Anthranil |
| 1.429 | >10 (82%) | 43.84 | Indole + Anthranil |
| 0.096 | 3.723 | >50 (21%) | 5-Chloroindole + Anthranil |

TABLE 7-continued

| MIC (ug/ml) | | | |
|---|---|---|---|
| MABA | LORA | IC50 | Feedstock |
| 0.074 | 2.952 | >50 (5%) | 6-Chloroindole + Anthranil |
| 0.293 | 4.53 | >50 (4%) | 4-Chloroindole + Anthranil |
| 0.137 | 1.499 | 10.33 | 4-Chloroindole + Anthranil |
| 0.15 | 1.833 | 20.83 | P1 |
| 1.157 | 9.755 | 33.5 | Indole + Anthranil |
| >10 (14%) | >10 (17%) | >50 (28%) | 4-Chloroindole + Anthranil |
| 0.285 | 2.286 | 30.13 | 7-Fluoroindole + Anthranil |
| 1.011 | >10 (89%) | >50 (21%) | 5-Chloroindole + Anthranil |

Activity of the products from the screening method was demonstrated with crude extracts and with highly purified compounds isolated from these extracts. Table 8 and 9 show that multiple products from multiple reactants possess antibacterial activity toward multiple types of bacteria.

TABLE 8

| Agar Plate Zone of Inhibition Assay (data in mm) | | |
|---|---|---|
| Starting substrate(s) | B. subtilis | M. smegmatis |
| Indole | 0 | 8 |
| Anthranil | 0 | 0 |
| Benzimidazole | 10 | 6 |
| 5-Fluoroindole | 20 | 15 |
| 6-Fluoroindole | 0 | 2 |
| Indole + Anthranil | 20 | 9 |
| Benzisoxazole + Indole | 0 | 15 |
| 7-Azaindole + Indole | 0 | 6 |
| 5-Fluoroindole + 6-Fluoroindole | 10 | 15 |
| 5-Fluoroindole + Indole | 7 | 15 |
| 6-Fluoroindole + Indole | 3 | 9 |
| 5-Fluoroindole + Anthranil | 15 | 16 |
| 6-Fluoroindole + Anthranil | 15 | 16 |

TABLE 9

| MIC (ug/ml) | | | |
|---|---|---|---|
| MABA | LORA | IC50 | Substrates |
| 0.576 | 5.444 | 46.21 | 4-fluoroindole + anthranil |
| 7.661 | >10 (70%) | 22.67 | 4-fluoroindole + anthranil |
| 3.891 | >10 (81%) | 42.81 | 4-fluoroindole + anthranil |
| 9.529 | >10 (0%) | 23.51 | Indole + benzisoxazole |
| 10 | >10 (0%) | >50 (6%) | Indole + Benzothiazole |
| 4.734 | >10 (80%) | >50 (17%) | 4-fluoroindole + anthranil |
| 0.133 | 4.079 | 11.8 | Indole + anthranil |
| 0.15 | 2.948 | >50 (0%) | 5-fluoroindole + anthranil |
| 9.916 | >10 (0%) | >50 (0%) | Indole + benzisoxazole |
| 0.304 | 2.452 | >50 (0%) | 6-fluoroindole + anthranil |
| 0.212 | 0.958 | 10.81 | 4-fluoroindole + anthranil |
| 3.921 | >10 (32%) | 44 | Indole + benzisoxazole |
| 1.94 | >10 (16%) | 41.74 | Indole + benzoxazole |
| 3.983 | >10 (33%) | 42.57 | 5-fluoroindole + anthranil |
| 4.144 | >10 (43%) | 43.48 | 7-fluoroindole + anthranil |
| 1.822 | 7.997 | <3.125 | 5-fluoroindole + anthranil |
| 0.61 | >10 (36%) | >50 (18%) | Indole + benzoxazole |
| 1.193 | >10 (38%) | >50 (4%) | 7-fluoroindole + anthranil |
| 4.726 | >10 (35%) | >50 (0%) | 5-fluoroindole + anthranil |
| 0.074 | 4.384 | 11.01 | Indole + benzoxazole |
| 0.136 | 7.684 | 18.46 | Indole + benzisoxazole |
| 0.105 | 4.868 | 11.69 | Indole + benzoxazole |
| 0.502 | >10 (85%) | >50 (31%) | Indole + benzoxazole |
| 0.177 | 3.78 | 21.28 | Indole + anthranil |
| 1.429 | >10 (82%) | 43.84 | Indole + anthranil |
| 0.096 | 3.723 | >50 (21%) | 5-chloroindole + anthranil |
| 0.074 | 2.952 | >50 (5%) | 6-chloroindole + anthranil |
| 0.293 | 4.53 | >50 (4%) | 4-chloroindole + anthranil |
| 0.137 | 1.499 | 10.33 | 4-chloroindole + anthranil |
| 0.15 | 1.833 | 20.83 | Indole + anthranil |

TABLE 9-continued

| MIC (ug/ml) | | | |
| --- | --- | --- | --- |
| MABA | LORA | IC50 | Substrates |
| 1.157 | 9.755 | 33.5 | indole + anthranil |
| >10 (14%) | >10 (17%) | >50 (28%) | 4-chloroindole + anthranil |
| 0.285 | 2.286 | 30.13 | 7-fluoroindole + anthranil |
| 1.011 | >10 (89%) | >50 (21%) | 5-chloroindole + anthranil |
| >50 | >50 | >50 | Indole + anthranil |
| 18.8 | >50 | >50 | 5-fluoroindole + anthranil |

Preparation of Recombinant Bacteria Containing Toluene Monooxygenases

The following is a procedure for preparing a recombinant microorganism that can oxidize substrates, such as indole, indole analogs, and mixtures thereof to generate candidate therapeutics. In particular, this example presents a procedure used to introduce the toluene monooxygenase genes from *P. mendocina* KR1 into *E. coli*. Unless otherwise noted, all molecular biological manipulations were performed by methods known to those skilled in the art, essentially as described by Sambrook et al. (Molecular Cloning, A Laboratory Manual, 2nd Edition, Cold Spring Harbor Laboratory Press, 1989). The DNA sequences of tmo A-E and tmo F from *P. mendocina* KR1 have been reported previously. (Yen et al., "Cloning and characterization of a *Pseudomonas mendocina* KR1 gene cluster encoding Toluene-4-Monooxygenase," *J. Bacteriol.* 173:5315-27, 1991; Yen and Karl, *J. Bacteriol.* 174:7253-61, 1992.) Total genomic DNA of *P. mendocina* KR1 was isolated using the method of Wilson (Wilson, 1993. p. 2.4.1 2.4.5. in F. M. Ausubel et al., (eds.), Current Protocols in Molecular Biology. Current Protocols, Brooklyn, N.Y.). The first five genes (tmo A-E) were amplified by using polymerase chain reaction (PCR) with primers TMOU 1 (5'-CG-GAATTCTTTAAACCCCACAGGCACGG-3') (SEQ ID NO:3) and TCED 3 (5'-GCGAATTCGATAATGGTTTG-CACTGCCA-3') (SEQ ID NO:4), which incorporated EcoRI restriction sites on each end of the 3652 bp amplified fragment. PCR was performed using a GeneAmp kit (Perkin Elmer, Foster City, Calif.) and reaction conditions recommended by the manufacturer. Cycling conditions were: 1 min at 94° C., 30 sec at 50° C., and 3 min at 71° C., for 25 cycles. Amplified DNA was digested with EcoRI (New England Biolabs, Beverly, Mass.), and ligated to similarly digested pUC18Not. The ligation mixture was used to transform *E. coli* JM109. Clones were selected by plating the cells onto LB agar-supplemented with ampicillin (100 μg/mL), and then replica plating onto LB plates that contained 100 μg/mL indole, and 20 μg/mL isopropyl-β-D-thiogalactopyranoside (IPTG). A single colony that formed a blue color from the conversion of indole to indigo, indicating monooxygenase activity, and contained the 3652 bp insert of tmo A-E, as determined by restriction analysis, was selected for further use and designated pRS184. (Ensley et al., *Science* 222:167-9, 1983; Yen et al., *J. Bacteriol.* 173:5315-27, 1991.)

To add the sixth gene encoding TMO F to the tmoA-E cluster, total chromosomal DNA of *P. mendocina* KR1 was digested with EcoRV and XmaI and separated on an agarose gel. Fragments ranging from 2 to 3 kb were excised from the gel, purified using the Qiaex system (Qiagen, Chatsworth, Calif.), ligated to similarly digested pRS184, and used to transform *E. coli* DH5a. Positive clones were selected for their ability to convert indole to indigo, as previously described. Restriction analysis of positive clones confirmed that they contained the 4727 bp tmoA-F insert. The plasmid construct was designated pRS184f (Pikus et al., *Biochemistry* 35:9106-19, 1996). The pRS184f construct was then digested with EcoRI and SmaI and the tmoA-F genes were ligated to similarly digested pVLT31 and used to transform *E. coli* DH5α, and *E. coli* DH10B. This plasmid was designated pRS202.

The same procedure can be used to prepare other recombinant microorganisms containing the toluene monooxygenase genes or similar genes which encode a non-heme diiron monooxygenase capable of oxidizing a carbon-carbon double bond to an epoxide. *Pseudomonas mendocina* ENVpmx1 (a toluene-4-monooxygenase deficient mutant of KR1) (McClay and R. J. Steffan, "Biosensor for TCE based on TCE-induced expression of toluene-4-monooxygenase from *Pseudomonas mendocina* KR1," Abstr. K36 page 348. In Abstracts of the 97th General meeting of the American Society of Microbiology 1997, Miami, Fla.), *Ralstonia pickettii* PKO1 (Byrne et al., "Sequence analysis of the gene cluster encoding toluene-3-monooxygenase form *Pseudomonas pickettii* PKO1," *Gene* 154:65-70, 1995), *Burkholderia cepacia* G4 (Shields et al., "Novel pathway of toluene catabolism in the trichloroethylene-degrading bacterium G4," *Appl. Environ. Microbiol.* 55:1624-1629, 1989), *Burkholderia* sp. strain ENVBF1 and *Pseudomonas* sp. strain ENVPC5 (McClay et al., "Chloroform mineralization by toluene-oxidizing bacteria," *Appl. Environ. Microbiol.* 62:2716-2722, 1996) were cultured overnight at 30° C. in shake flasks containing basal salts medium (BSM) supplemented with 0.4% sodium glutamate. Toluene was included in the vapor phase of the cultures when induction of the toluene oxygenases was desired. Prior to substrate degradation assays the cultures were harvested by centrifugation and resuspended in BSM to an optical density of 2 at 550 nm ($OD_{550}$). A standard curve of optical density versus protein concentration for each strain was used to calculate the amount of protein per mL of the resuspended cultures. *Escherichia coli* DH10B containing the plasmid pRS202 (Pikus et al., "Changes in the regiospecificity of aromatic hydroxylation produced by active site engineering in the diiron enzyme toluene 4-monooxygenase," *Biochemistry* 36:9283-9289, 1997) was prepared in a similar manner, except that the strain was grown at 37° C. in LB media, and was resuspended to an $OD_{550}$ of 4 in LB media with 0.3-1 mM IPTG to induce expression of T4MO.

Site-Directed Mutagenesis of $Ile_{100}$ (I100)

Crystallographic studies of MMO led to the hypothesis that homologue of the T4MO residue I100 (L110 in MMO) functions as part of a "gate" that controls the access of reactants and products to and from the catalytic center on the MMO hydroxylase (Rosenzweig et al., *Proteins,* 29:141-52, 1997). When the catalytic center is in the oxidized form the "gate" is closed, whereas it is open when the diiron center is reduced. This action can control the timing of the reactants entering the active site to prevent the larger organic substrates from binding in the active site before diatomic oxygen is bound and activated. Premature entry of organic substrates could interfere with the activation of $O_2$, thereby inhibiting catalysis. Alternately, I100 could function as a clamp, holding the substrate in close proximity to the diiron center, ensuring proper orientation of the intended substrate.

Three mutations were made at this site; I100A, I100C, and I100V, as disclosed in U.S. Pat. No. 7,169,591, which is incorporated by reference herein in its entirety. The R side chain of the mutant I100C is 28% smaller, and more polar, than the wild type isoleucine. This isoform efficiently converted indole to indigo, as indicated by the rapid production of an intense blue color on LB media, but it decreased activity towards toluene (Table 4). The isoform I100R was inactive. These results support the gating hypothesis proposed by Rosenzwieg et al., *Proteins,* 29:141-2, 1997. By making the side chain of this residue longer and charged, oxygenase activity was abolished, possibly because the side chain was too large to allow entrance of reactants regardless of the position of the gate. When the side chain was decreased in size (i.e., I100C), the enzyme remained active, but the level of activity of the isoform towards the substrates tested was decreased relative to the wild-type enzyme. With the smaller residue in this position, more small organic molecules can enter the active site prematurely and block activation of $O_2$. Alternately, the smaller, polar residue may not be able to hold and/or orient the small, primarily hydrophobic substrates in the active site. The smaller residue had a lesser effect on the oxidation of a larger substrate, indigo.

Site-Directed Mutagenesis of $Gly_{103}$ (G103)

Amino acid alignments comparing MMO and two AMO sequences revealed that, as the size of the residue in the position homologous to G103 of T4MO increases (glycine, alanine, valine), so does the enantio-selectivity of propene oxidation (Zhou et al., "The alkene monooxygenase from *Xanthobacter* PY2 is a binuclear non-heme iron protein closely related to toluene-4-monooxygenase," *FEBS Lett.* 430:181-5, 1998). T4MO and MMO have the smallest possible amino acid in this position (glycine), whereas T2MO has a larger residue (leucine).

Three mutations were made at this site; G103L, G103I, and G103V, as disclosed in U.S. Pat. No. 7,169,591. *E. coli* containing plasmid pRS184f (G103L) (ATCC PTA-107) was deposited with the ATCC on May 21, 1999.

Site-Directed Mutagenesis of $Ala_{107}$ (A107)

The alanine residue at position 107 in the T4MO hydroxylase is conserved in all of the monooxygenases studied, suggesting that it confers some evolutionary advantage in these diiron monooxygenases. The hydrophobic alanine was replaced with the longer and more polar cystein, serine, and threonine residues. Results from experiments in U.S. Pat. No. 7,169,591, suggest that the conserved alanine at positions corresponding to 107 in T4MO is somehow involved in positioning substrates in the active sites.

Three mutations were made at this site; A107S, A107C, and A107T, as disclosed in U.S. Pat. No. 7,169,591. *E. coli* containing plasmid pRS184f (A107S) (ATCC PTA-106) was deposited with the ATCC on May 21, 1999.

Site-Directed Mutagenesis of $Gln_{141}$ (Q141)

The residue in MMO homologous to Q141 in T4MO is a cysteine which is believed to be important in the process of methane oxidation (Zhou et al., "The alkene monooxygenase from *Xanthobacter* PY2 is a binuclear non-heme iron protein closely related to toluene-4-monooxygenase," *FEBS Lett.* 430:181-5, 1998). The hydrogen of the cysteine sulfhydril group can be removed at some step in the catalytic cycle, leaving a cysteine radical that facilitates the hydroxylation of methane (Feig et al., *Chem. Rev.* 94:759-805, 1994). With the exception of T2MO, the aromatic oxygenases have a glutamine at this position, while T2MO and the alkene monooxygenases have acidic residues. It has been proposed that the absence of a cysteine at this position accounts for inability of the aromatic and alkene monooxygenases to oxidize unsaturated hydrocarbon methane (Zhou et al., *FEBS Lett.* 430:181-5, 1998), in spite of the fact that T4MO is known to oxidize CF, 1,2-DCA, and the unsaturated methyl groups of toluene and xylene (Pikus et al., *Biochemistry,* 36:9283-9, 1997; McClay et al., *Appl. Environ. Microbiol.* 62:2716-22, 1996). To mimic the hydroxylase of MMO, the mutations Q141C, Q141V, and Q141E were created, as disclosed in U.S. Pat. No. 7,169,591. Neither of these mutations allowed T4MO to oxidize methane, but the Q141C mutation did affect the oxidation of a number of aromatic compounds (Pikus et al., *Biochemistry* 36:9283-9, 1997). Both the Q141C and Q141V mutations decreased the size and dipole moment of the R chain, relative to the wild type. The result of both mutations was an overall relaxed specificity observed in the hydroxylase.

Site Directed Mutagenesis of $Phe_{176}$ (F176)

Another residue whose position suggested a gating function was F176 (F188 in MMO) (Rosenzweig et al., *Proteins* 29:141-52, 1997). In U.S. Pat. No. 7,169,591, two substitutions were made at this position to probe the significance of this residue. The mutant F176A catalyzed the very slow formation of indigo, but was inactive towards all other substrates tested, whereas the F176I mutant was much more active than F176A, but it accumulated low levels of indigo relative to mutant I100C. The results of these experiments suggest that F176 is an important residue in the active site complex. Making the residue smaller either abolished activity completely, or it resulted in a great decrease in toluene oxidizing activity. Toluene is presumably the natural substrate for T4MO, and toluene oxidation is very regio-specific, with the primary reaction product being para-cresol (Pikus et al., *Biochemistry* 36:9283-9, 1997). Even slight changes in the active site spatial conformation could alter docking of the substrate, thereby either inhibiting oxidation, or resulting in a change in the regio-specificity of oxidation.

Site-Directed Mutagenesis of $Phe_{196}$ (F196)

In T4MO the residue F196 is located adjacent to Q197. In MMO the amino acid analogous to Q197 participates in the binding of the iron atoms that make up the catalytic center of the enzyme. In the related diiron enzymes in plants, fatty acid desaturase and fatty acid hydroxylase, the difference in the catalytic activity of the two enzymes is dictated by the active site geometry (Broun et al., *Science* 282:1315-7, 1998). Subtle differences impacting the coordination of the diiron center, or the distance-maintained between the substrate and the catalytic center are believed to dictate whether these enzymes function as desaturases or hydroxylases. Because of its proximity to the diiron center, altering F196 can lead to changes in catalytic activity (Zhou et al., *Appl. Environ. Microbiol.* 65:1589-95, 1999).

Three mutations were generated at site F196; F196I, F196Y, and F196L, as disclosed in U.S. Pat. No. 7,169,591. The F196L mutant had a significant level of activity. Although similar to the F176I isoform, it had a reduced capacity for indigo formation; forming pinkish/purple colonies instead of the dark purple colonies of the wild type. The F196L mutation did have a measurable effect on CF oxidation. In initial assays with F196L and the wild type T4MO clones, cells were grown and incubated with CF in LB broth. Both the wild type enzyme and the F196L mutant degraded toluene immediately, but CF degradation did not occur until after a lag period of approximately 40 minutes, and it proceeded at a greater rate than achieved with the wild-type isoform. When the amount of CF degraded by the wild type isoform was compared to the amount of toluene degraded by the same strain, there was a linear correlation. CF degradation, however, was completely inhibited during the initial period of the incubation, but it was linear after the lag period.

The inhibition of CF degradation seen with the F196L isoform when assayed in LB media is similar to the apparent competitive inhibition of CF degradation observed when strain KR1 was incubated with both TCE and CF (McClay et al., *Appl. Environ. Microbiol.*, 62:2716-22, 1996). Furthermore, in LB broth cultures, indigo does not appear to form in the presence of toluene, but it did form in cultures with chloroform, suggesting that indole interferes with CF degradation, but not toluene oxidation.

When we performed the same assays in minimal media to prevent the formation of indole from LB, the F196L isoform degraded CF much more rapidly than the wild type isoform. The F196L isoform oxidizing 15.9 μmol toluene and 348 nmol CF compared to the 15.1 μmol toluene and 201 nmol CF degraded by the wild type isoform.

Site-Directed Mutagenesis of $Thr_{201}$ (T201)

Like residue A107, all of the diiron oxygenases considered had a threonine at the position analogous to the T201 of T4MO. It has been proposed that this threonine is required for the active scission of the O=O bond. This hypothesis was explored in U.S. Pat. No. 7,169,591, where T201 was replaced with a series of amino acids, including serine (T201S). The substitution of threonine with a serine decreases the bulk of the R chain, leaving room for greater mobility of the substrates in the active site, but retaining the hydroxy group thought to be involved in $O_2$ activation. Previous results suggest that the T201 residue of T4MO is involved in positioning substrates in the active site.

Site-Directed Mutagenesis of Other Amino Acids in the Active Site of T4MO

Four other amino acid residues in the active site of T4MO were mutated. The mutation L192M substituted a larger amino acid for the native residue. Like the mutations F176A and F196G discussed above, mutations to two active site residues, I224V/A and I227T, decreased the activity of the oxygenase. All four of these mutants produced low levels of indigo, but generally lacked the ability to oxidize any of the other substrates tested (Table 4). One exception was the I227T isoform, which retained a low level of TCE oxidation activity (Table 4). Since this mutant failed to oxidize toluene, the TCE ratio of this mutant was infinitely large.

Site-Directed Mutagenesis of Amino Acid Residues Outside of the Active Site of T4MO Two residues that were not located within the active site of T4MO were mutated. Because of the positioning of the residue V102, it probably does not come into direct contact with T4MO substrates. However it is located between two potentially important residues (I100 and G103) discussed above. The native valine was replaced with the more polar residue threonine to determine if small perturbations in this region of the alpha-helix would be communicated to the active site. The isoform, V102T, remained highly active on all substrates (Table 8). Also, the TCE ratio of the V102T isoform was 70% of wild type (Table 8). The residues homologous to N222 in T4MO are serines or threonines in the oxygenases examined here, with the exception of the AMO of PY2 which also has an asparagine. The mutations N222S and N222Q were created to determine if this residue performs an important function. The mutant N222S has a TCE ratio of 10.3 and a butadiene ratio of 0.059 (Table 4), both decreased relative to the wild type, but the mutation did not alter enantio-selectivity of butadiene oxidation (Table 4). The mutant N222Q incorporates an R chain that has the same functional group as the wild type asparagine, but is longer by one carbon, and is inactive. Since the chemical properties of the mutated R-chains that result in an inactive isoform are the similar to those of the native residue, whereas the active mutant isoform has a different functional group, it appears that size of the amino acid at this position effects catalytic activity. Perhaps the increase in the bulk of the R chain of N222Q causes a distortion in the a-helical bundles, while the decreased size of the R chain of the mutant N222S residue allows a more normal conformation, thereby preserving activity.

TABLE 8

| Mutation | Change in side chain size | Change dipole characteristic | μM Toluene degraded | nM TCE degraded | | Indigo formation |
|---|---|---|---|---|---|---|
| Wild type | NA | NA | 8.6 (0.03) | 134 (8.8) | N = 7$_c$ | ++ |
| I100K | increase | NP > charged | xx | xx | | -- |
| I100C | decrease | NP > polar | 1.69 (0.4) | 88 (4.4) | N = 4 | ++ |
| V102T | increase | NP > polar | 8.8 (0.11) | 92 (4.7) | N = 2 | ++ |
| G103L | increase | none | 3.2 (0.47) | 0.0 | N = 4 | ++ |
| A107S | increase | NP > polar | 7.7 (0.48) | 139 (3.5) | N = 6 | ++ |
| Q141V | decrease | charged > NP | 2.66 (0.59) | 46 (6.4) | N = 4 | ++ |
| Q141C | decrease | Charged > polar | 7.03 (0.29) | 147 (0.83) | N = 4 | ++ |
| F176L | decrease | none | 2.2 (0.07) | 150 (2.9) | N = 5 | ++ |
| F176A | decrease | none | xx | xx | | ++ |
| I180F | increase | none | nd | nd | N = 2 | ++ |
| I192M | increase | none | 4.7 (0.69) | 197 (1.2) | N = 2 | ++ |
| F194P | decrease | none | xx | xx | | -- |
| F196L | decrease | none | 6.8 (0.09) | 157 (10) | N = 4 | ++ |
| F196G | decrease | none | xx | xx | | +/- |
| T201S | decrease | none | 8.7 (0.21) | 138 (1.6) | N = 7 | ++ |
| T201A | decrease | Polar > NP | nd | nd | | ++ |
| T201F | increase | Polar > NP | nd | nd | | ++ |
| T201Q | increase | Polar > charged | nd | nd | | ++ |
| F205I | decrease | none | nd | nd | N = 2 | ++ |
| N222S | decrease | Charged > Polar | 9.1 (0.03) | 94 (3.3) | N = 2 | ++ |
| N222Q | increase | None | xx | xx | | -- |

TABLE 8-continued

| Mutation | Change in side chain size | Change dipole characteristic | μM Toluene degraded | nM TCE degraded | | Indigo formation |
|---|---|---|---|---|---|---|
| I224V/A | decrease | None | xx | xx | | +/− |
| I224F | increase | None | 9.08 (0.16) | 171 (12) | N = 2 | ++ |
| I227T | decrease | NP > Polar | 0 | 17 (0) | | ++ |
| Q238I | decrease | Charged > NP | 8.1 (0.06) | 185 (2.4) | N = 2 | ++ |

NP = non-polar

```
                          SEQUENCE LISTING

SEQ ID NO: 1 toluene-4-monooxygenase gene cluster, complete sequence
   1 aagcttttaa accccacagg cacggagaac aagaatatgg cgatgcaccc acgtaaagac
  61 tggtatgaac tgaccagggc gacaaattgg acacctagct atgttaccga agagcagctt
 121 ttcccagagc ggatgtccgg tcatatgggt atcccgctgg aaaaatggga aagctatgat
 181 gagccctata agacatccta tccggagtac gtaagtatcc aacgtgaaaa ggatgcaggt
 241 gcttattcgg tgaaggcggc acttgagcgt gcaaaaattt atgagaactc tgacccaggt
 301 tggatcagca cttttgaaatc ccattacggc gccatcgcag ttggtgaata tgcagccgta
 361 accggtgaag gtcgtatggc ccgttttttca aaagcaccgg gaaatcgcaa catggctacg
 421 tttggcatga tggatgaact gcgccatggc cagttacagc tgttttttccc gcatgaatac
 481 tgtaagaagg atcgccagtt tgattgggca tggcgggcct atcacagtaa cgaatgggca
 541 gccattgctg caaagcattt ctttgatgac atcattaccg gacgtgatgc gatcagcgtt
 601 gcgatcatgt tgacgttttc attcgaaacc ggcttcacca acatgcagtt tcttggttg
 661 gcggcagatg ccgcagaagc aggtgactac acgtttgcaa acctgatctc cagcattcaa
 721 accgatgagt cgcgtcatgc acaacagggc ggccccgcat acagttgct gatcgaaaac
 781 ggaaaaagag aagaagccca aaagaaagtc gacatggcaa tttggcgtgc ctggcgtcta
 841 tttgcggtac taaccgggcc ggttatggat tactacacgc cgttggagga ccgcagccag
 901 tcattcaagg agtttatgta cgagtggatc atcggacagt tcgaacgctc gttgatagat
 961 ctgggcttgg acaagccctg gtactgggat ctattcctca aggatattga tgagcttcac
1021 catagttatc acatgggtgt ttggtactgg cgtacaaccg cttggtggaa ccctgctgcc
1081 ggggtcactc ctgaggagcg tgactggctg aagaaaaagt atccaggatg gaataaacgt
1141 tggggtcgtt gctgggatgt gatcaccgaa aacgttctca atgaccgtat ggatcttgtc
1201 tctccagaaa ccttgcccag cgtgtgcaac atgagccaga taccgctggt aggtgttcct
1261 ggtgatgact ggaatatcga agtttttcagt cttgagcaca atgggcgtct ttatcatttt
1321 ggctctgaag tggatcgctg ggtattccag caagatccgg ttcagtatca aaatcatatg
1381 aatatcgtcg accgcttcct cgcaggtcag atacagccga tgactttgga aggtgccctc
1441 aaatatatgg gcttccaatc tattgaagag atgggcaaag acgcccacga ctttgcatgg
1501 gctgacaagt gcaagcctgc tatgaagaaa tcggcctgat aaattgagga atagaaatg
1561 tcggcatttc cagttcacgc agcgtttgaa aaagatttct tggttcaact ggtagtggtg
1621 gatttaaatg attccatgga ccaggtagcg gagaaagttg cctaccattg tgttaatcgt
1681 cgtgttgctc ctcgtgaagg tgtcatgcgg gttcgaaagc atagatcaac tgagctattt
1741 ccacgggata tgaccatagc tgagagcggc cttaacccaa ctgaagtgat cgatgtggta
1801 ttcgaggagt agcgaaaatg agctttgaaa aaatctgttc cctcgacgat atctgggtag
1861 gcgaaatgga gactttcgag acgtccgatg gtaccgaagt cttaatcgtc aacagtgaag
```

```
                              SEQUENCE LISTING 1921  agcatggagt gaaggcctac caggcgatgt gcccccatca ggagattctg ttatctgaag 1981  gtagctacga aggtggagta attacatgcc gcgctcacct atggaccttc aatgacggaa 2041  cagggcatgg catcaaccca gatgactgtt gtcttgccga atatcctgta gaggtaaaag 2101  gcgatgatat ttacgtcagt acaaaaggca ttttaccgaa taaggcacac agctaaacct 2161  gcgctagttg ttaaatccca catcagcgaa gcggctggga aaagaaggat aatgtgatga 2221  gcacattggc tgatcaggct ttacataaca ataacgttgg accgattatc cgtgctggtg 2281  atctcgtgga accagtgatt gaaacagctg aaatcgataa tccgggaaaa gagatcacag 2341  ttgaagatag gcgggcttat gtacgcatcg cagcagaagg cgaactgata ttgactcgaa 2401  aaaccttgga gagcagttg gtcgcccgt caacatgca ggaactagaa atcaatctgg 2461  cgtcctttgc aggacagatc caagccgacg aagaccagat tcgcttctac tttgataaaa 2521  ccatgtaagg agggcaccat gagctttgaa tccaagaaac cgatgcgtac atggagccac 2581  ctggccgaaa tgagaaagaa gccaagtgag tacgatattg tctcacgcaa gcttcactac 2641  agtaccaaca atcccgattc accctgggag ctgagccccg atagcccaat gaatctgtgg 2701  tacaagcagt accgtaacgc atcgccattg aaacacgata actgggatgc ttttactgat 2761  cctgaccaac ttgtataccg cacctacaac ctgatgcagg atggtcagga atcttatgtg 2821  cagagtctgt tcgatcaatt caatgagcgc gaacatgacc aaatggtgcg ggagggctgg 2881  gagcacacaa tggcccgctg ttattccccg ttgcgctatc tgttccactg cctgcagatg 2941  tcgtcggcct atgttcagca gatggcgccg gcgagcacaa tctcaaattg ctgcatcctt 3001  caaactgctg acagcctgcg atggttgacg cacaccgcct accgaacgca cgaactcagt 3061  cttacttatc cggatgctgg ttcaggtgag cacgagcgag aactgtggga gaaagagccg 3121  ggttggcagg gctgcgtga attgatggag aagcaactaa ctgcttttga ttggggagag 3181  gcttttgtca gtctaaattt ggcggtcaag ccaatgattg tcgagagtat tttcaaacca 3241  ctgcagcagc aagcatggga aaataacgat accttgcttc ctctgttgat tgacagtcag 3301  ctgaaagatg ccgagcgtca tagtcgttgg tcgaaagcac ttgtaaaaca tgcgctggaa 3361  aaccccgata atcacgctgt aattgaaggt tggattgaaa agtggcgccc cttggctgac 3421  agggcagctg aagcttacct gagtatgcta tctagcgaca tcttgcccgc tcaatatctt 3481  gagcgtagta cctcattgag ggcatccata cttacggtct gattacgcgc cgtttgggtc 3541  ctattggtgg gtcttcccct tcggcattgc tgaagggggc ttttagagac gttatctatg 3601  ttcaatattc aatcggatga tcccctgcac cattttgagg cggatagtaa tgacactcta 3661  cttagtgctg ctctacgtgc tgaattggta tttccatatg agtgtaactc aggagggtgc 3721  ggcgcatgta agatcgagct gcttgaggga gaggtctcta acctatggcc tgatgcacca 3781  ggattagccg cccgtgaact ccgtaagaat cgttttttgg cgtgccagtg caaaccatta 3841  tccgacctca aaattaaggt cattaaccgt gcggagggac gtgcttcaca tcccccaaa 3901  cgttcctcga ctcgagtagt tagtaagcgc ttcctctctg acgagatgtt tgagctgcga 3961  cttgaagcga aacagaaagt ggtgttttca ccagggcaat attttatggt tgacgtgcct 4021  gaactcggca ccagagcata ctccgcggca aaccctgttg atggaaacac actaacgctg 4081  atcgtaaaag cagtgccgaa tgggaaggta tcctgcgcac tcgcaaatga aactattgaa 4141  acacttcagt tggatggtcc ttacgggctg tcagtattaa aaactgcgga tgaaactcaa
```

```
4201 tccgtcttta tcgctggggg gtcaggtatc gcgccgatgg tgtcgatggt gaatacgctg 4261 attgcccaag ggtatgaaaa accgattacg gtgttttacg gttcacggct agaagctgaa 4321 ctggaagcgg ccgaaaccct gtttgggtgg aaagaaaatt taaaactgat taatgtgtcg 4381 tcgagcgtgg tgggtaactc ggagaaaaag tatccgaccg gttatgtcca tgagataatt 4441 cctgaataca tggaggggct gctaggtgcc gagttctatc tgtgcggccc gccgcagatg 4501 attaactccg tccagaagtt gcctatgatt gaaaataaag taccgttcga agcgattcat 4561 tttgataggt tcttttaaaa ttaataagca atagttggtt ttagtagaat tttcagtggc 4621 gtaatgtcgg cgctaaggaa ctcc SEQ ID NO: 2 wild type tmoA subunit
MAMHPRKDWYELTRATNWTPSYVTEEQLFPERMSGHMGIPLEKWESYDEPYKTSYPEYVSIQRE

KDAGAYSVKAALERAKIYENSDPGWISTLKSHYGAIAVGEYAAVTGEGRMARFSKAPGNRNMAT

FGMMDELRHGQLQLFFPHEYCKKDRQFDWAWRAYHSNEWAAIAAKHFFDDIITGRDAISVAIML

TFSFETGFTNMQFLGLAADAAEAGDYTFANLISSIQTDESRHAQQGGPALQLLIENGKREEAQK

KVDMAIWRAWRLFAVLTGPVMDYYTPLEDRSQSFKEFMYEWIIGQFERSLIDLGLDKPWYWDLF

LKDIDELHHSYHMGVWYWRTTAWWNPAAGVTPEERDWLEEKYPGWNKRWGRCWDVITENVLNDR

MDLVSPETLPSVCNMSQIPLVGVPGDDWNIEVFSLEHNGRLYHFGSEVDRWVFQQDPVQYQNHM

NIVDRFLAGQIQPMTLEGALKYMGFQSIEEMGKDAHDFAWADKCKPAMKKSA

SEQ ID NO: 3 primer TMOU 1
CGGAATTCTTTAAACCCCACAGGCACGG

SEQ ID NO: 4 primer TCED 3
GCGAATTCGATAATGGTTTGCACTGCCA
```

What is claimed is:

1. A method of preparing and identifying an extract that modulates the growth or replication of a microorganism, the method comprising the steps of:
(a) incubating a first compound and a second compound in the presence of at least one oxygenase to produce the extract;
wherein the first and second compounds are independently selected from the group consisting of indole, indene, isoindoline, 2-azaindole, 3-azaindole, 4-azaindole, 5-azaindole, 6-azaindole, 7-azaindole, benzimidazole, benzamidazoline, imidazopyridine, 4-azabenzamidazole, 5-azabenzamidazole, 6-azabenzamidazole, anthranil, benzisoxazole, and benzoxazole, benzofuran, benzothiophene, benzothiazole, benzoisothiophene, quinoline, isoquinoline, and quinozoline; optionally substituted with at least one —OH, —CH$_3$, —NH$_2$, —NO$_2$, —F, —Cl, or —Br substituents;
wherein the at least one oxygenase comprises a toluene monooxygenase;
(b) contacting the microorganism with the extract; and
(c) determining a level of growth or replication of the microorganism;
wherein a difference in the level of growth or replication of the microorganism as compared to the level in a control identifies that the extract modulates the growth or replication of the microorganism.

2. The method of claim 1, wherein the first and second compounds are independently selected from the group consisting of mono- or poly-substituted indole, indene, isoindoline, 2-azaindole, 3-azaindole, 4-azaindole, 5-azaindole, 6-azaindole, 7-azaindole, benzimidazole, benzamidazoline, imidazopyridine, 4-azabenzamidazole, 5-azabenzamidazole, 6-azabenzamidazole, anthranil, benzisoxazole, benzoxazole, benzofuran, benzothiophene, benzothiazole, benzoisothiophene, quinoline, isoquinoline, and quinozoline; substituted with at least one —OH, —CH$_3$, —NH$_2$, —NO$_2$, —F, —Cl, or —Br substituents.

3. The method of claim 1, wherein the microorganism is a bacterium, virus, fungus, or protozoan.

4. The method of claim 1, wherein the microorganism is a Gram positive or Gram negative bacterium.

5. The method of claim 1, wherein the microorganism is *M. smegmatis* or *B. subtilis*.

6. The method of claim 1, wherein the microorganism is *M. tuberculosis*.

7. The method of claim 1, wherein the microorganism is multidrug resistant or extensively drug resistant *M. tuberculosis*.

8. The method of claim 1, wherein the oxygenase is a toluene-4-monooxygenase.

9. The method of claim 1, wherein the method further comprises the steps of:
generating one or more test compounds, wherein the first compound is oxidized by the at least one oxygenase to generate at least one first oxidized product, and the second compound is oxidized by the at least one oxygenase to generate at least one second oxidized product; further wherein the at least one first oxidized product and the at least one second oxidized product react to generate one or more test compounds;
wherein the first compound is indole optionally substituted with at least one —OH, —CH$_3$, —NH$_2$, —NO$_2$, —F, —Cl, or —Br substituents, and the second compound is selected from the group consisting of indole, indene, isoindoline, 2-azaindole, 3-azaindole, 4-azaindole, 5-azaindole, 6-azaindole, 7-azaindole, benzimidazole, benzamidazoline, imidazopyridine, 4-azabenzamidazole, 5-azabenzamidazole, 6-azabenzamidazole, anthranil, benzisoxazole, and benzoxazole, benzofuran, benzothiophene, benzothiazole, benzoisothiophene, quinoline, isoquinoline, and quinozoline; optionally substituted with at least one —OH, —CH$_3$, —NH$_2$, —NO$_2$, —F, —Cl, or —Br substituents;

contacting the microorganism with the one or more test compounds; and determining a level of growth or replication of the microorganism;

wherein a difference in the level of growth or replication of the microorganism as compared to the level in a control identifies that the one or more test compounds modulate the growth or replication of the microorganism.

10. A method of preparing and identifying a test compounds that modulate the growth or replication of a microorganism, the method comprising the steps of:

(a) incubating a first compound and a second compound in the presence of at least one oxygenase to produce an extract;

wherein the first compound is indole optionally substituted with at least one —OH, —CH$_3$, —NH$_2$, —NO$_2$, —F, —Cl, or —Br substituents, and the second compound is selected from the group consisting of indole, indene, isoindoline, 2-azaindole, 3-azaindole, 4-azaindole, 5-azaindole, 6-azaindole, 7-azaindole, benzimidazole, benzamidazoline, imidazopyridine, 4-azabenzamidazole, 5-azabenzamidazole, 6-azabenzamidazole, anthranil, benzisoxazole, and benzoxazole, benzofuran, benzothiophene, benzothiazole, benzoisothiophene, quinoline, isoquinoline, and quinozoline; optionally substituted with at least one —OH, —CH$_3$, —NH$_2$, —NO$_2$, —F, —Cl, or —Br substituents;

wherein the at least one oxygenase comprises a toluene monooxygenase;

(b) generating one or more test compounds within the extract, wherein the first compound is oxidized by the at least one oxygenase to generate at least one first oxidized product, and the second compound is oxidized by the at least one oxygenase to generate at least one second oxidized product; further wherein the at least one first oxidized product and the at least one second oxidized product react to generate one or more test compounds;

(c) contacting the microorganism with the extract;

(d) determining a level of growth or replication of the microorganism;

wherein a difference in the level of growth or replication of the microorganism as compared to the level in a control identifies that the extract modulates the growth or replication of the microorganism;

(e) isolating the one or more test compounds from the extract;

(f) contacting the microorganism with the one or more test compounds; and (g) determining a level of growth or replication of the microorganism;

wherein a difference in the level of growth or replication of the microorganism as compared to the level in a control identifies that the test compound that modulates the growth or replication of the microorganism.

* * * * *